US008729227B2

(12) United States Patent
Balasubramaniam

(10) Patent No.: US 8,729,227 B2
(45) Date of Patent: May 20, 2014

(54) COMPOUNDS FOR CONTROL OF APPETITE

(75) Inventor: Ambikaipakan Balasubramaniam, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 1063 days.

(21) Appl. No.: 12/056,600

(22) Filed: Mar. 27, 2008

(65) Prior Publication Data

US 2009/0227519 A1 Sep. 10, 2009

Related U.S. Application Data

(62) Division of application No. 11/333,889, filed on Jan. 18, 2006, now abandoned.

(51) Int. Cl.
*C07K 7/00* (2006.01)
(52) U.S. Cl.
USPC .............. 530/329; 530/327; 514/4.9; 514/5.2
(58) Field of Classification Search
USPC ............. 514/4.8, 5.2, 21.5, 4.9; 530/329, 327
See application file for complete search history.

(56) References Cited

U.S. PATENT DOCUMENTS

| | | | |
|---|---|---|---|
| 3,842,067 | A | 10/1974 | Sarantakis |
| 3,862,925 | A | 1/1975 | Sarantakis |
| 3,972,859 | A | 8/1976 | Fujino et al. |
| 4,105,603 | A | 8/1978 | Vale, Jr. et al. |
| 4,244,946 | A | 1/1981 | Rivier et al. |
| 4,297,346 | A | 10/1981 | Rips et al. |
| 4,415,558 | A | 11/1983 | Vale, Jr. et al. |
| 4,870,009 | A | 9/1989 | Evans et al. |
| 5,270,302 | A | 12/1993 | Shiosaki et al. |
| 5,328,899 | A | 7/1994 | Boublik et al. |
| 5,410,018 | A | 4/1995 | Spindel et al. |
| 5,604,203 | A | 2/1997 | Balasubramaniam |
| 5,993,843 | A | 11/1999 | Sakurada et al. |
| 6,013,633 | A | 1/2000 | Balasubramaniam et al. |
| 6,046,167 | A | 4/2000 | Balasubramaniam et al. |
| 6,235,718 | B1 | 5/2001 | Balasubramaniam et al. |
| 6,737,408 | B1 | 5/2004 | Balasubramaniam et al. |
| 6,913,892 | B1 | 7/2005 | Bard et al. |
| 6,962,902 | B2 | 11/2005 | Balasubramaniam et al. |
| 2004/0122033 | A1 | 6/2004 | Nargund et al. |
| 2006/0287242 | A1 | 12/2006 | Ewing et al. |

FOREIGN PATENT DOCUMENTS

| | | |
|---|---|---|
| AU | 15263 | 11/1988 |
| EP | 0268297 A2 | 5/1988 |
| EP | 0288965 A2 | 11/1988 |
| EP | 0381340 A2 | 8/1990 |
| WO | 91/03494 A1 | 3/1991 |
| WO | 2006/036770 A2 | 4/2006 |
| WO | 2006/091506 A2 | 8/2006 |

OTHER PUBLICATIONS

Fehrentz et al., An Efficient Synthesis of Optically Active a-(t-Butoxycarbonylamino)-aldehydes from a-Amino Acids, Communications, Aug. 1983, pp. 676-678.
Adrian et al., Human Distribution and Release of a Putative New Gut Hormone, Peptide YY, Gastroenterology, vol. 89, 1985, pp. 1070-1077.
Balasubramaniam et al., Syntheses and Receptor Affinities of Partial Sequences of Peptide YY (PYY), Peptide Research, vol. 1, No. 1, 1988, pp. 32-35.
Cox et al., The effects of neuropeptide Y and its fragments upon basal and electrically stimulated ion secretion in rat jejunum mucosa, Br. J. Pharmacol., vol. 101, 1990, p. 247-252.
Cox et al., The Effects of Selective Amino Acid Substitution Upon Neuropeptide Y Antisecretary Potency in Rat Jejunum Mucosa, Peptides, vol. 12, 1991, pp. 323-327.
Ekblad et al., Projections of Peptide-Containing Neurons in Rat Small Intestine, Neuroscience, vol. 20, No. 1, 1987, pp. 169-188.
Friel et al., Neuropeptide Y: a powerful modulator of epithelial ion transport, Br. J. Pharmac., vol. 88, 1986, pp. 425-431.
Goumain et al., The Peptide YY-Preferring Receptor Mediating Inhibition of Small Intestinal Secretion is a Peripheral Y2 Receptor: Pharmacological Evidence and Molecular Cloning, Molecular Pharmacology, vol. 60, No. 1, 2001, pp. 124-134.
Laburthe et al., Interaction of Peptide YY with Rat Intestinal Epithelial Plasma Membranes: Binding of the Radioiodinated Peptide, Endocrinology, vol. 118, No. 5, 1986, pp. 1910-1917.
Laburthe, Peptide YY and Neuropeptide Y in the Gut: Availability, Biological Actions, and Receptors, TEM, vol. 1, 1990, pp. 168-174.
Lundberg et al., Localization of Peptide YY (PYY) in Gastrointestinal Endocrine Cells and Effects on Intestinal Blood Flow and Motility, Proc. Natl. Acad. Sci. USA, vol. 79, 1982, pp. 4471-4475.
MacFadyen et al., NPY Stimulates Nett Absorption Across Rat Intestinal Mucosa in Vivo, Neuropeptides, vol. 7, 1986, pp. 219-227.
Playford et al., Preliminary Report: Role of Peptide YY in Defence Against Diarrhoea, The Lancet, vol. 335, 1990, pp. 1555-1557.
Tatemoto, Neuropeptide Y: Complete Amino Acid Sequence of the Brain Peptide, Proc. Natl. Acad. Sci. USA, vol. 79, 1982, pp. 5485-5489.
Valet et al., Neuropeptide Y and Peptide YY Inhibit Lipolysis in Human and Dog Fat Cells Through a Pertussis Toxin-Sensitive G Protein, J. Clin. Invest. vol. 85, 1990, pp. 291-295.
Voisin et al., Peptide YY Receptors in the Proximal Tubule PKSV-PCT Cell Line Derived from Transgenic Mice, The Journal of Biological Chemistry, vol. 268, No. 27, 1993, pp. 20547-20554.
Asakawa et al., Characterization of the Effects of Pancreatic Polypeptide in the Regulation of Energy Balance, Gastroenterology, vol. 124, 2003, pp. 1325-1336.

(Continued)

*Primary Examiner* — David Lukton
(74) *Attorney, Agent, or Firm* — Wood, Herron & Evans, LLP

(57) ABSTRACT

This invention relates generally to neuropeptide Y ("NPY") $Y_4$ receptor agonists including pancreatic polypeptide (PP), analogs thereof, and peptide fragments of PP, e.g. PP(32-36), and analogs thereof, to pharmaceutical compositions containing such $Y_4$ receptor agonists, and to methods for treatment of mammals using the same. The NPY $Y_4$ receptor agonists may be administered to mammals either alone or in combination with NPY $Y_2$ receptor agonists including peptide YY (PYY) (3-36), analogs thereof, and to peptide fragments of PYY(3-36), e.g. PYY(22-36) and PYY(25-36), and analogs thereof, such as to control food intake in mammals, blood pressure, cardiovascular response, libido, circadian rhythm, hyperlipidimia, chronic pancreatitis, and nonalcoholic fatty liver disease including nonalcoholic steatohepatitis.

5 Claims, 2 Drawing Sheets

(56) References Cited

OTHER PUBLICATIONS

Balasubramaniam et al., Neuropeptide Y Family of Hormones: Receptor Subtypes and Antagonists, Peptides, vol. 18, No. 3, 1997, pp. 445-457.
Balasubramaniam, Neuropeptide Y (NPY) Family of Hormones: Progress in the Development of Receptor Selective Agonists and Antagonists, Current Pharmaceutical Design, vol. 9, 2003, pp. 1165-1175.
Balasubramaniam et al., Bis(31/31') {[Cys31, Trp32, Nva34] NPY-(31-36)}: A Specific NPY Y-1 Receptor Antagonists, Journal of Medical Chemistry, vol. 39, No. 4, 1996, pp. 811-813.
Baldock et al., Hypothalamic Y2 Receptors Regulate Bone Formation, J. Clin. Invest., vol. 109, No. 7, 2002, pp. 915-921.
Batterham et al., Pancreatic Polypeptide Reduces Appetite and Food Intake in Humans, J. Clin. Endocrinol. & Metab., vol. 88, No. 8, 2003, pp. 3989-3992.
Beck-Sickinger et al., A novel cyclic analog of neuropeptide Y specific for the Y2 receptor, Eur. J. Biochem., vol. 206, 1992, pp. 957-964.
Berglund et al., Recent Development in Our Understanding of the Physiological Role of PP-Fold Peptide Receptor Subtypes, Ex. Biol. med., vol. 228, 2003, pp. 217-244.
Bhatnagar et al., Structure-Activity Relationships of Novel Hematoregulatory Peptides, J. Med. Chem., vol. 39, 1996, pp. 3714-3819.
Daniels et al., High-affinity neuropeptide Y receptor antagonists, Proc. Natl. Acad.Sci. USA, vol. 92, 1995, pp. 9067-9071.
Ekstrand et al., Deletion of neuropeptide Y (NPY) 2 receptor in mice results in blockage of NPY-induced angiogenesis and delayed wound healing, Proc. Natl. Acad. Sci. USA, vol. 100, No. 10, 2003, pp. 6033-6038.
Jois et al., Conformation of neuropeptide Y receptor antagonists: structural implications in receptor selectivity, Peptides, vol. 24, 2003, pp. 1035-1043.
Korner et al., To Eat or Not to Eat—How the Gut Talks to the Brain, N. Eng. J. Med., vol. 349, No. 10, 2003, pp. 926-928.
Krstenansky et al., Centrally truncated and stabilized porcine neuropeptide Y analogs: Design synthesis, and mouse brain receptor binding, Proc. Natl. Acad. Sci. USA, vol. 86, 1989, pp. 4377-4381.
Lassmann et al., Low Plasma Levels of Pancreatic Polypeptide in Obesity, Diabetes, vol. 29, 1980, pp. 428-430.
Marco et al., Reduced Pancreatic Polypeptide Secretion in Obese Subjects, J. Clin. Endocrinol & Metab., vol. 50, No. 4, 1980, pp. 744-747.
Marsh et al., Role of the Y5 neuropeptide Y receptor in feeding and obesity, Nature Medicine, vol. 4, No. 6, 1998, pp. 718-721.
Marsh et al., Role of Y5 neuropeptide Y receptor in limbic seizures, Proc. Natl. Acad. Sci, USA, vol. 96, No. 23, 1999, pp. 13518-13523.
McLean et al., Examination of the Role of the Amphipathic a-Helix in the Interaction of Neuropeptide Y and Active Cyclic Analogues with Cell Membrane Receptors and Dimyristoylphosphatidylcholine, Biochemistry, vol. 29, 1990, pp. 2016-2022.
McLean et al., Lipid and Membrane Interactions of Neuropeptide Y, Biochimica et Biophysica Acta, vol. 1024, 1990, pp. 1-4.
Moran, Pancreatic Polypeptide: More Than Just Another Gut Hormone?, Gastroenterology, vol. 124, No. 5, 2003, pp. 1542-1544.
Naveilhan et al., Normal feeding behavior, body weight and leptin response require the neuropeptide Y Y2 receptor, Nat. Med., vol. 5, No. 10, 1999, pp. 1188-1193.
Parker et al., GR23118(1229U91) and other analogues of the C-terminus of neuropeptide Y are potent neuropeptide Y Y1, receptor antagonists and neuropeptide Y Y4 receptor agonists, Eur. J. Pharmacol, vol. 349, 1998, pp. 97-105.
Parker et al., Neuropeptide Y receptors as targets for anti-obesity drug development: perspective and current status, Eur. J. Pharmacol, vol. 440, 2002, pp. 173-187.
Pedrazzini et al., Cardiovascular response, feeding behavior and locomotor activity in mice lacking the NPY Y1 receptor, Nat. Med., vol. 4, No. 6, 1998, pp. 722-726.
Sainsbury et al., Y4 receptor knockout rescues fertility in ob/ob mice, Genes Dev., vol. 16, 2002, pp. 1077-1088.
Sainsbury et al., Synergistic Effects of Y2 and Y4 Receptors on Adiposity and Bone Mass Revealed in Double Knockout Mice, Mol. Cell. Biol., vol. 23, No. 15, 2003, pp. 5225-5233.
Small et al., Gut Hormones as Peripheral Anti Obesity Targets, Current Drug Targets—CNS & Neurological Disorders, vol. 3, 2004, pp. 379-388.
Smith-White et al., Cardiac function in neuropeptide Y Y4 receptor-knockout mice, Regulatory Peptides, vol. 110, 2002, pp. 47-54.
Ueno et al., Decreased Food Intake and Body Weight in Pancreatic Polypeptide-Overexpressing Mice, Gastroenterology, vol. 117, 1999, pp. 1427-1432.
Uhe et al., Potential regulators of feeding behavior in anorexia nervosa, Am. J. Clin. Nutr., vol. 55, 1992, pp. 28-32.
Whitcomb et al., Distribution of pancreatic polypeptide receptors in the rat brain, Brain Research, vol. 760, 1997, pp. 137-149.
Zukowska et al., Neuropeptide Y: A Novel Mechanism for Ischemic Angiogenesis, Trends Cardiovasc. Med., vol. 13, No. 2, 2003, pp. 86-92.
S.L. Parker et al., Agonist interalization by cloned Y1 neuropeptide Y (NPY) receptor in Chinese hamster ovary cells shows strong preference for NPY, endosome-linked entry and fast receptor recycling, Regulatory Peptides, 2002, vol. 107, pp. 49-62.
Balasubramaniam, Clinical Potentials of Neuropeptide Y Family of Hormones, The American Journal of Surgery 183 (2002), 430-434.
Balasubramaniam et al., Structure-Activity Studies Including a (CH2-NH) Scan of Peptide YY (PYY) Active Site, PYY(22-36), for Interaction with Rat Intestinal PYY Receptors: Development of Analogues with Potent in Vivo Activity in the Intestine, Journal of Medical Chemistry 2000, 43, 3420-3427.
Litvak et al., Characterization of Two Novel Proabsorptive Peptide YY Analogs, BIM-43073D and BIM-43004C, Digestive Diseases and Sciences, vol. 44, No. 3 (Mar. 1999), pp. 643-648.
Batterham et al., Gut Hormone PPY3-36 Physiologically Inhibits Food Intake, Nature, vol. 418, Aug. 2002, www.nature.com/nature.
Batterham et al., Inhibition of Food Intake in Obese Subjects by Peptide YY3-36, The New England Journal of Medicine, 349:10, www.nejm.org, Sep. 4, 2003.
Balasubramaniam et al., Characterization of Neuropeptide Y Binding Sites in Rat Cardiac Ventricular Membranes, Peptides, vol. 11, 1990, pp. 545-550.
Balasubramaniam et al., Synthesis and Biological Properties of 4-Norleucine-neuropeptide Y; Secondary Structure of Neuropeptide Y, Biochimica et Biophysica Acta, vol. 997, 1989. pp. 176-181.
Barnes et al., The Fine Structure of Continuous Human Neuroblastoma Lines SK-N-SH, SK-N-BE(2), and SK-N-MC, In Vitro, vol. 17, No. 7, Jul. 1981, pp. 619-631.
Bickel et al., Synthesis and Bioactivity of Monobiotinylated DALDA: A Mu-Specific Opioid Peptide Designed for Targeted Brain Delivery, The Journal of Pharmacology and Experimental Therapeutics, vol. 268, No. 2, 1994, pp. 791-796.
Bleakman et al., Neuropeptide Y Inhibits Ca2+ Influx Cultured Dorsal Root Ganglion Neurones of the Rat via a Y2 Receptor, Department of Pharmacological and Physiological Sciences, University of Chicago, Mar. 11, 1991, pp. 1781-1789.
Chance et al, Pertussis Toxin Inhibits Neuropeptide Y-Induced Feeding in Rats, Peptides, vol. 10, 1989, pp. 1283-1286.
Cheung et al., N-Methylamino Acids in Peptide Synthesis. V. The Synthesis of N-tert-butyloxycarbonyl, N-methylamino Acids by N-methylation, Can J. Chem., vol. 55, 1997, pp. 906-910.
Grundemar et al., Characterization of Receptor Types for Neuropeptide Y and Related Peptides, The Biology of Neuropeptide Y and Related Peptides, Humana Press, 1993, pp. 197-239.
Coy et al., Solid Phase Reductive Alkylation Techniques in Analogue Peptide Bond and Side-Chain Modification, Tetrahedron, vol. 44, No. 3, 1988, pp. 835-841.
De Wied (Ed), Neuropeptides, Basics and Perspectives, Elsevier Science Publishers, The Netherlands, 1990, Chap. V-IX.
Dumont et al., Neuropeptide Y and Neuropeptide Y Receptor Subtypes in Brain and Peripheral Tissues, Progress in Neurobiology, vol. 38, 1992, pp. 125-167.

(56) References Cited

OTHER PUBLICATIONS

Flood et al., Dissociation of the Effects of Neuropeptide Y on Feeding and Memory: Evidence for Pre- and Postsynaptic Mediation, Peptides, vol. 10, 1989, pp. 963-966.
Freidinger et al., Synthesis of 9-Fluorenylmethyloxycarbonyl-Protected N-Alkyl Amino Acids by Reduction of Oxazolidinones, J. Org. Chem., vol. 48, 1983, pp. 77-81.
Fuhlendorff et al., [Leu31, Pro 34] Neuropeptide Y; A Specific Y1 Receptor Agonist, Biochemistry, Proc. Natl. Acad. Sci. USA, vol. 87, Jan. 1990, pp. 182-186.
Glover et al., Conformational Studies on the Pancreatic Polypeptide Hormone Family, Eur. J. Biochem, vol. 142, 1985, pp. 379-385.
Gordon et al., Characterization of Functional Neuropeptide Y Receptors in a Human Neuroblastoma Cell Line, Journal of Neurochemistry, International Society for Neurochemistry, 1990, pp. 506-513.
Gross et al, (Eds.), The Peptides, vol. 1, Academic Press, Inc., New York, London, 1979, 26-52, 125-126, 156-174, 242-260, 293-304, 336-362.
Gross et al., (Eds.), The Peptides, vol. 3, Academic Press, Inc. New York, London, 1981, 1-99, 101-136, 203-252.
Heilig et al., Neuropeptide Y: An Overview of Central Distribution, Functional Aspects, and Possible Involvement in Neuropsychiatric Illnesses, Acta Phychiatr. Scad., vol. 82, 1990, 95-114.
Hinson et al., Neuropeptide Y Stimulates Inositol Phospholipid Hydrolysis in Rat Brain Miniprisms, Brain Research, vol. 446, 1988, pp. 379-382.
IUPAC-IUB Commission on Biochemical Nomenclature A One-Letter Notation for Amino Acid Sequences Tentative Rules, The Journal of Biological Chemistry, vol. 243, No. 13, Jul. 10, 1968, pp. 3557-3559.
Lundberg et al., Neuropeptide Y Receptor in Pig Spleen: Binding Characteristics, Reduction of Cyclick AMP Formation and Calcium Antogonist Inhibition of Vasoconstriction, European Journal of Pharmacology, vol. 145, 1988, pp. 21-29.
Merrifield, Solid Phase Peptide Synthesis, I. The Synthesis of a Tetrapeptide, J. Am. Chem. Soc., vol. 85, Jul. 20, 1963, pp. 2149-2154.
Michel, Receptors for Neuropeptide Y: Multiple Subtypes and Multiple Second Messengers, TIPS, vol. 12, Oct. 1991, pp. 389-394.
Mihara et al., Neuropeptide Y-Induced Intracellular Ca2+ Increases in Vascular Smooth Muscle Cells, FEBS Letters, vol. 259, No. 1, Dec. 1989, pp. 79-82.
Motulsky et al., Neuropeptide Y Mobilizes Ca2+ and Inhibits Adenylate Cyclase in Human Erythroleukemia Cells, Amer. J. of Physiological Society, 1988, pp. E880-E885.
Pardridge et al., Endorphin Chimeric Peptides: Transport Through the Blood-Brain Barrier in Vivo and Cleavage of Disulfide Linkage by Brain, Endocrinology, vol. 126, No. 2, 1990, p. 977-984.
Poste et al., Lipid Vesicles as Carriers for Introducing Biologically Active Materials into Cells, Methods in Cell Biology, vol. XIV, Academic Press, New York, NY, 1976, pp. 33-71.
Reymond et al., Truncated, Branched, and/or Cyclic Analogues of Neuropeptide Y: Importance of the Pancreatic Peptide Fold in the Design of Specific Y2 Receptor Ligands, J. Med. Chem., vol. 35, 1992, pp. 3653-3659.
Rodriguez et al., Synthesis and Biological Activities of Pseudopeptide Analogues of the C-Terminal Heptapeptide of Cholecystokinin. On the Importance of the Peptide Bonds, J. Med. Chem., vol. 30, 1987, pp. 1366-1373.
Sasaki et al., Solid Phase Synthesis of Peptides Containing the CH2NH Peptide Bond Isostere, Peptides, vol. 8, 1987, pp. 119-121.
Schroder et al., Methods of Peptide Synthesis, The Peptides, Academic Press, 1965, pp. 72-75.
Schwartz et al., Signal Epitopes in the Three-Dimensional Structure of Neuropeptide Y Interaction with Y1, Y2, and Pancreatic Polypeptide Receptors, Annals of New York Academy of Sciences, vol. 611, 1990, pp. 35-47.
Sheikh et al., Localization of Y1 Receptors for NPY and PYY on Vascular Smooth Muscle Cells in Rat Pancreas, American Physiological Society, 1991, G250-G257.
Sheikh et al., Structural Characterization of Y1 and Y2 Receptors for Neuropeptide Y and Peptide YY by Affinity Cross-Linking, J. Biol. Chem., vol. 265, No. 14, May 15, 1990, pp. 8304-8310.
Sheikh et al., Y2-Type Receptors for Peptide YY on Renal Proximal Tubular Cells in the Rabbit, American Physiological Society, 1989, pp. F978-F984.
Unden et al., Neuropeptide Y Receptor in the Rat Brain, Eur. J. Biochem., vol. 145, FEBS 1984, pp. 525-530.
Wahlestedt et al., Evidence for Different Pre- and Post-Junctional Receptors for Neuropeptide Y and Related Peptides, Regulatory Peptides, vol. 13, 1986, pp. 307-318.
Walker et al., 125I-Neuropeptide Y and 125I-Peptide YY Bind to Multiple Receptor Sites in Rat Brain, Molecular Pharmacology, vol. 34, Sep. 8, 1988, pp. 779-792.
Westlind-Danielson et al., Neuropeptide Y Receptors and the Inhibition of Adenylate Cyclase in the Human Frontal and Temporal Cortex, Neuroscience Letters, vol. 74, 1987, pp. 237-242.
Wilson, MD, et al., Harrison's Principles of Internal Medicine, 12th Ed., McGrawHill, Inc., New York, NY, 1991, Chap. 15, 65-67, 69, 75-76, 84-86, 151, 182, 185, 190, 196, 301, 316-317, 319, 321-322, 369, 371-372.

COMPOUNDS FOR CONTROL OF APPETITE

CROSS-REFERENCE TO RELATED APPLICATIONS

This application is a divisional of U.S. patent application Ser. No. 11/333,889, filed Jan. 18, 2006, now abandoned, the disclosure of which is hereby incorporated by reference herein.

STATEMENT REGARDING FEDERALLY SPONSORED RESEARCH

The U.S. Government has a paid-up license in this invention and the right in limited circumstances to require the patent owner to license others on reasonable terms as provided for by the terms of Grant/Contract No. GM47122-08S1 awarded by the National Institutes of Health.

FIELD OF THE INVENTION

This invention relates generally to neuropeptide Y ("NPY") $Y_4$ receptor agonists including pancreatic polypeptide (PP), analogs thereof and to peptide fragments of PP, and analogs thereof, and to methods for treatment of mammals using the same and, more specifically, the invention is directed to NPY $Y_4$ receptor agonists including PP(32-36), and analogs thereof, to pharmaceutical compositions containing such pentapeptides, and to methods of treatment of mammals using such pentapeptides. The NPY $Y_4$ receptor agonists may be administered to mammals either alone or in combination with NPY $Y_2$ receptor agonists including peptide YY (PYY) (3-36), analogs thereof, and to peptide fragments of PYY(3-36), and analogs thereof, such as to control food intake in mammals.

BACKGROUND OF THE INVENTION

Obesity is a major disorder affecting as much as one third of the North American population. Several studies have shown that such individuals are at increased risk in developing cardiovascular disease (hypertension and hyper-cholesterolemia), diabetes and several types of cancer. The effective treatment of obesity, however, remains a largely unachieved goal. Existing pharmaco-therapeutic approaches to weight loss involve the use of amphetamine-based agents such as amphetamine, diethylpropion, mazindol and fenfluramine which act directly on the central nervous system ("CNS") to lower food intake by modulating dopaminergic, adrenergic and/or serotonergic mechanisms. Although weight loss can be achieved with such agents, their use is restricted due to CNS side-effects, potential addiction liability and the production of tolerance to their actions, with chronic administration leading to potential depression, vestibular disturbances, hallucinations and addiction, as well as interference with the actions of other drugs, such as MAO inhibitors and antihypertensives. There is also a subpopulation of obese patients that is refractory to present anorectic drug treatments. The medical need is high for an effective anorectic agent that overcomes the above disadvantages of existing therapies. Of particular need are agents which act by alternative mechanisms to modulate food intake and/or metabolism.

Throughout this application, various publications are referenced. The disclosure of these publications is hereby incorporated by reference into this application to describe more fully the art to which this invention pertains.

Neuropeptide Y ("NPY")

Neuropeptides are small peptides originating from large precursor proteins synthesized by peptidergic neurons and endocrine/paracrine cells. They hold promise for treatment of neurological, psychiatric, and endocrine disorders (De Wied, D. In: Neuropeptides: Basics and Perspectives (Elsevier, Amsterdam-New York-Oxford), 1990). Often the precursors contain multiple biologically active peptides. There is great diversity of neuropeptides in the brain caused by alternative splicing of primary gene transcripts and differential precursor processing. The neuropeptide receptors serve to discriminate between ligands and to activate the appropriate signals. Thus, it is expected that the receptors for neuropeptides consist of a large number of members.

Neuropeptide Y (NPY), a 36-amino acid peptide, is the most abundant neuropeptide to be identified in mammalian brain. Human NPY has the formula: H-Tyr-Pro-Ser-Lys-Pro-Asp-Asn-Pro-Gly-Glu-Asp-Ala-Pro-Ala-Gfu-Asp-Met-Ala-Arg-Tyr-Tyr-Ser-Ala-Leu-Arg-His-Tyr-Ile-Asn-Leu-Ile-Thr-Arg-Gln-Arg-Tyr-NH2 (SEQ. ID. NO. 1). Porcine and rat NPY have the same sequence except for Leu instead of Met in the 17-position.

NPY is an important regulator in both the central and peripheral nervous systems (Heilig, M. and E. Widerlov. Neuropeptide Y: an overview of central distribution, functional aspects, and possible involvement of neuropsychiatric illnesses. Acta Psychiatr. Scand. 82:95-114 (1990)) and influences a diverse range of physiological parameters, including effects on psychomotor activity, food intake, central endocrine secretion, and vasoactivity in the cardiovascular system. High concentrations of NPY are found in the sympathetic nerves supplying the coronary, cerebral, and renal vasculature and has contributed to vasoconstriction. NPY binding sites have been identified in a variety of tissues, including spleen (Lundberg, J. M., A. Hemsen, O. Larsson, A. Rudehill, A. Saria, and B. Fredholm. Neuropeptide Y receptor in pig spleen: binding characteristics, reduction of cyclic AMP formation and calcium antagonist inhibition of vasoconstriction. Bur. J. Pharmacol. 145:21-29 (1988)), intestinal membranes, brain (Hinson, J., C. Rauh, and J. Coupet. Neuropeptide Y stimulates inositol phospholipid hydrolysis in rat brain microprisms. Brain Response. 446:379-382 (1988)), aortic smooth muscle (Mihara, S. Y. Shigeri, and M. Fujimoto. Neuropeptide Y-induced intracellular Ca2+ increase in vascular smooth muscle cells. FEBS Lett. 259: 79-82 (1989)), kidney, testis, and placenta (Dumont, Y., J. C. Martel, A. Fournier, S. St.-Pierre, and R. Quiron. Neuropeptide Y and neuropeptide Y receptor subtypes in brain and peripheral tissues. Prog. Neurobiol. 38:125-167 (1992)). In addition, binding sites have been reported in a number of rat and human cell lines (e.g. Y1 in SK-N-MC, MC-IXC, CHP-212, and PC12 cells; Y2 in SK-N-Be(2), CHP-234, and SMS-MSN) (Grundemar, L., S. P. Sheikh, and C. Wahlestedt; In: The Biology of Neuropeptide Y and Related Peptides. (Humana Press, Inc., Totawa, N.J.), (1992)).

NPY forms a family (called the pancreatic polypeptide family) together with pancreatic polypeptide (PP) and peptide YY (PYY) which all consist of 36 amino acids and have a common tertiary structure, the so-called PP-fold (Glover, I. D., D. J. Barlow, J. E. Pitts, S. P. Wood, I. J. Tickle, T. L. Blundell, K. Tatemoto, J. R. Kimmel, A. Wollmer, W. Strassburger, and Y.-S. Zhang. Conformational studies of the pancreatic polypeptide hormone family. Eur. J. Biochem. 142: 379-385 (1985)). Specific features of this family include a polyproline helix in residues 1 through 8, beta-turn in residues 9 through 14, an alpha-helix in residues 15 through 30, an outward-projecting C-terminus in residues 30 through 36, and a carboxy terminal amide (Schwartz, T. W., J. Fuhlendorff, L. L. Kjems, M. S. Kristensen, M. Vervelde, M. O'Hare, J. L. Kristenansky, and B. Bjornholm. Signal epitopes in the three-dimensional structure of neuropeptide Y. Ann. N.Y. Acad. Sci. 611:35-47 (1990)). The C-terminal amidated residue of these peptides appears to be essential for biological activity (Wahlestedt et at, 1986). Studies with peptide fragments of NPY have indicated that multiple NPY receptor subtypes exist (Wahlestedt, C., N. Yanaihara, and R. Hakanson, Evidence for different pre- and postjunctional receptors for neuropeptide Y and related peptides. Regal. Pept. 13:307-318 (1986)). Specifically, six receptor subtypes, denoted as Y1 Y2, Y3, Y4, Y5, and Y6, are understood to mediate the actions of NPY with each to-date, except for Y3, having been cloned.

The Y1, Y2, Y4, and Y5 receptors have been proposed to regulate feeding behavior, i.e. food intake, in subjects. A key pharmacological feature which distinguishes Y1 from Y2 is the fact that the Y1 receptor (and not the Y2 receptor) responds to an analog of NPY modified at residues 31 and 34 ([Let31,Pro34]NPY), whereas the Y2 receptor (and not the Y1 receptor) has high affinity for the NPY peptide carboxyl-terminal fragment NPY-(18-36)(Fuhlendorff, J., U. Cether, L. Aakerlund, N. Langeland-Johansen, H. Thogersen, S. G. Melberg, U. B. Olsen, O. Thastrup, and T. W. Schwartz. [Leu31,Pro34]Neuropeptide Y: A specific Y1 receptor agonist. Proc. Natl. Acad. Sci. USA 87:182-186 (1990)). NPY analogs and N-terminally-shortened fragments, e.g. NPY(18-36), which contain one or more specific D-isomer substitutions for the naturally occurring residues (as well as pharmaceutically acceptable salts thereof), dispersed in a pharmaceutically acceptable liquid or solid carrier, can be administered to mammals, including humans, to substantially lower blood pressure over an extended period of time or to counteract hypertension.

Experimental and clinical observations also have supported the concept that neuropeptides play central roles in neurotransmission as well as the regulation of secretory functions of adenohypophysial, pancreatic, adrenalcortical and gut cells. Among the thirty or so neuropeptides that have been implicated in neuronal function in the mammalian central nervous system, several have also been suggested to function as neurotransmitters or neuromodulators primarily in afferent neurons.

An additional action of NPY is to decrease cardiac contractility (inotropy). This is an extremely important action of NPY, because it is known that, under many circumstances in which inotropy is decreased, diseases of life-threatening importance, e.g. congestive heart failure and cardiogenic shock, are associated with probable increased release of NPY into the blood. Prevention of NPY release, using a presynaptic NPY agonist, or NPY's action, using a postsynaptic NPY antagonist, may be beneficial in these disease states.

NPY has also been reported to produce coronary artery vasoconstriction and thereby may decrease myocardial blood flow resulting in myocardial ischemia. Such a circumstance can result in angina pectoris or, under more severe circumstances, may result in myocardial infarction and death. In recent years, several classes of drugs have proven effective in dilating coronary arteries to prevent such events.

Peptide YY ("PYY")

Peptide YY (PYY) is a 36-residue peptide amide isolated originally from porcine intestine, and localized in the endocrine cells of the gastrointestinal tract and pancreas (Tatemoto et al. Proc. Natl. Acad. Sci. 79:2514, 1982). Peptide YY has N-terminal and C-terminal tyrosine amides; accordingly, these two tyrosines give PYY its name (Y represents the amino acid tyrosine in peptide nomenclature). In addition, PYY shares a number of central and peripheral regulatory roles with its homologous peptide Neuropeptide Y (NPY), which was originally isolated from porcine brain (Tatemoto, Proc. Natl. Acad. Sci. 79:5485, 1982). PYY is localized in intestinal cells; NPY, in contrast, is present in the submucous and myenteric neurons that innervate the mucosal and smooth muscle layers, respectively (Ekblad et al. Neuroscience 20:169, 1987). Both PYY and NPY are believed to inhibit gut motility and blood flow (Laburthe, Trends Endocrinol. Metab. 1: 168, 1990), and they are also thought to attenuate basal (Cox et al. Br. J. Pharmacol. 101:247, 1990; Cox et al. J. Physiol. 398:65, 1988; Cox et al. Peptides 12:323, 1991; Friel et al. Br. J. Pharmacol. 88:425, 1986) and secretatogue-induced intestinal secretion in rats (Lundberg et al. Proc. Natl. Acad. Sci USA 79:4471, 1982; Playford et al. Lancet 335: 1555, 1990) and humans (Playford et al., supra), as well as stimulate net absorption (MacFadyen et al. Neuropeptides 7:219, 1986). Elevated plasma PYY levels have been reported in individuals suffering from several conditions that cause diarrhea (Adrian et al. Gastroenterology 89:1070, 1985). Taken together, these observations suggest that PYY and NPY are released into the circulation after a meal (Adrian et al. Gastroenterology 89:1070, 1985: Balasubramaniam et al. Neuropeptides 14:209, 1989), and, thus may play a physiological role in regulating intestinal secretion and absorption, serving as natural inhibitors of diarrhea.

A high affinity PYY receptor system that exhibits a slightly higher affinity for PYY than NPY has been characterized in rat intestinal epithelia (Laburthe et al. Endocrinology 118: 1910, 1986; Laburthe, Trends Endocrinol. Metabl. supra) and shown to be negatively coupled to adenylate cyclase (Servin et al. Endocrinology 124:692, 1989). Consistently, PYY exhibited greater antisecretory potency than NPY in voltage clamped preparations of rat small intestine (Cox et al. J. Physiol supra), while C-terminal fragments of NPY were found to be less effective in their antisecretory potency than PYY (Cox et al. Br. J. Pharmacol, supra), Structure-activity studies using several partial sequences have led to the identification of PYY(22-36) as the active site for interacting with intestinal PYY receptors (Balasumbramaniam et al. Pept. Res. 1:32, 1988). This intestinal PYY-preferring receptor has now been cloned and shown to be identical to the $Y_2$ receptors cloned from the brain (Goumain et al. Mol Pharmacol 60:124-134, 2001).

In addition, PYY has been implicated in a number of physiological activities including nutrient uptake (see, e.g., Bilcheik et al. Digestive Disease Week 506:623, 1993), cell proliferation (see, e.g., Laburthe, Trends Endocrinol. Metab. 1:168, 1990; Voisin et al. J. Bio. Chem., 1993), lipolysis (see, e.g., Valet et al. J. Clin. Invest. 85:291, 1990), and vasoconstriction (see, e.g., Lundberg et al., Proc. Natl. Acad. Sci, USA 79:4471, 1982).

The amino acid sequences of porcine and human PYY are as follows:

(SEQ. ID. NO. 2)
porcine PPY: YPAKPEAPGEDASPEELSRYYASLRHYLNLVTRQRY, (SEQ. ID. NO. 3)
human PYY: YPIKPEAPGEDASPEELNRYYASLRHYLNLVTRQRY.

The amino acid sequences for dog PYY and for rat PYY are the same as that of porcine PYY.

With respect to PYY, it has been reported previously that peripheral administration of PYY(3-36), a NPY $Y_2$-preferring ligand, can on peripheral administration attenuate food intake in normal and fasted mice and rats as well as in normal and obese humans (Nature 418:650-654; 2002, N Engl J Med 349:941-948; 2003). The anorexigenic actions of PYY(3-36) are suggested to be mediated by arcuate nucleus $Y_2$ receptors. One advantage of using Y2 selective ligands is that they can suppress the food intake on peripheral administration, whereas Y1 and Y5 selective ligands, as described above, have to penetrate the BBB to modulate food intake.

In addition to interacting with the Y2 receptor, PYY(3-36) can potently activate Y4 and Y5 receptors. Consequently, the inventor previously developed Y2 receptor selective agonists that are based on PYY(22-36) and PYY(25-36) (See U.S. Pat. Nos. 5,604,203, and 6,046,167 to Balasubramaniam) which are devoid of activities at the other NPY receptors including Y1, Y4, and Y5 at concentrations up to 20,000 nM. Preferred PYY(25-36) analogs include N-α-Ac-[Trp$^{30}$]PYY(25-36)-NH$_2$ (SEQ. ID. NO. 4), referred to as BWX-115, N-α-Ac-[Trp$^{27}$,ψ$^{35/36}$]PYY(25-36)-NH$_2$ (SEQ. ID. NO. 5), referred to as BT-56, and N-α-Ac-[Trp$^{30}$,ψ$^{35/36}$]PYY(25-36)-NH$_2$ (SEQ. ID. NO. 6), referred to as BT-123, and the PYY(22-36) analog N-α-Ac[Nle$^{24,28}$,Trp$^{30}$,Nva$^{31}$,ψ$^{35/36}$]PYY(22-36)-NH$_2$ (SEQ. ID. NO. 7), referred to as B-48, [wherein ψ in the foregoing formulas is —CH2-NH—] which can be used to control food intake in animals and humans.

Pancreatic Peptide ("PP")

Pancreatic peptide (PP) is a 36-amino-acid secretory peptide that is predominantly produced by the pancreas and released in response to nutrient stimuli.

The amino acid sequence of human PP is as follows:

(SEQ. ID. NO. 8)
APLEPVYPGDNATPEQMAQYAADLRRYINMLTRPRY.

PP, like PYY, shares a number of central and peripheral regulatory roles with its homologous peptide NPY. It has been reported recently that PP can attenuate body weight increase in mice through inhibiting food intake and increasing energy expenditures (Gastroenterology 124:1325-1336; 2003). These actions are mediated by altering the expression of orexigenic (NPY, orexin & ghrelin downregulated) and anorexigenic (urocortin upregulated) peptides, and decreasing gastric emptying and activity of the vagovagal or vago-sympathetic reflex arc. In addition, the anorectic effects of PP have been suggested to be mediated by the $Y_4$ receptors in the area postrema (AP) because: a) autoradiography following peripheral administration of PP revealed high accumulation of PP in AP; b) expression of c-fos is seen in AP following iv administration of PP; and c) high density of $Y_4$ receptors are present in AP (Brain Res 760:137-149; 1997).

one advantage of using Y4 selective ligands, like the Y2 selective ligand, is that they can suppress the food intake on peripheral administration, whereas Y1 and Y5 selective ligands, as described above, have to penetrate the BBB to modulate food intake. Native PP may not be an ideal candidate for suppressing food intake because of its short half-life of about six minutes and its interactions with Y5 receptors.

Accordingly, it would be desirable to develop NPY $Y_4$ receptor agonists that can be used alone or mixed with NPY $Y_2$ receptor agonists, as disclosed in U.S. Pat. Nos. 5,604,203, and 6,046,167 to Balasubramaniam, which are herein incorporated by reference, for controlling an NPY mediated physiological response in a subject, such as to control food intake in mammals, and that are expected to prove useful in the treatment of weight problems (e.g. obesity and diabetes), eating disorders, and such.

SUMMARY OF THE INVENTION

This invention is directed to neuropeptide Y ("NPY") $Y_4$ receptor agonists including pancreatic polypeptide (PP), ana-logs thereof, and peptide fragments of PP, e.g. PP(32-36), and analogs thereof, to pharmaceutical compositions containing such $Y_4$ receptor agonists, and to methods for treatment of mammals using the same. The NPY $Y_4$ receptor agonists may be administered to mammals either alone or in combination with NPY $Y_2$ receptor agonists including peptide YY (PYY) (3-36), analogs thereof, and to peptide fragments of PYY(3-36), e.g. PYY(22-36) and PYY(25-36), and analogs thereof, as disclosed in U.S. Pat. Nos. 5,604,203, and 6,046,167 to Balasubramaniam, which are herein incorporated by reference, such as to control food intake in mammals, blood pressure, cardiovascular response, libido, circadian rhythm, hyperlipidimia, chronic pancreatitis, and nonalcoholic fatty liver disease including nonalcoholic steatohepatitis.

Accordingly, in one aspect, the present invention features NPY $Y_4$ receptor agonists of PP(32-36) and analogs thereof, such pentapeptide analogs having the formula:

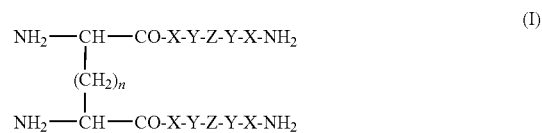

wherein:
each X, independently, is an aromatic amino acid;
each Y, independently, is an amino acid having a guanidino group;
each Z, independently, is an aliphatic amino acid;
n=1, 2, 3 or 4; and
wherein the compound optionally includes one or two pseudopeplide bonds where each pseudopeptide bond is independently selected from —CH$_2$NH—, —CH$_2$—S—, —CH$_2$CH$_2$—, —CH$_2$—O— and CH$_2$—CO—.

A preferred compound of formula (I) includes,

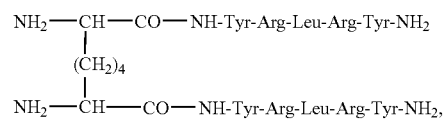

(which is referred to as B-74).

In another aspect, the present invention features pentapeptide analogs of PP(32-36) having the formula:

wherein.
each X, independently, is an aromatic amino acid;
each Y, independently, is an amino acid having a guanidino group;
each Z, independently, is an aliphatic amino acid;
A1 and A2, independently, are selected from Cys, Pen, Glu, Asp, Lys, and Dpr; and
wherein the compound optionally includes one or two pseudopeptide bonds where each pseudopeptide bond is independently selected from —CH$_2$—NH—, —CH$_2$S—, —CH$_2$—C$_2$—, —CH$_2$—O— and CH$_2$—CO—.

A preferred compound of formula (II) includes,

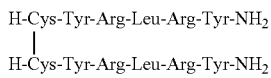

In another aspect, the present invention features pentapeptide analogs of PP(32-36) having the formula:

$$H—[X—Y—Z—Y—X]_n—NH_2 \quad (III)$$

wherein:
each X, independently, is an aromatic amino acid;
each Y, independently, is an amino acid having a guanidino group;
each Z, independently, is an aliphatic amino acid;
n=1, 2, 3 or 4; and
wherein the compound optionally includes one or two pseudopeptide bonds where each pseudopeptide bond is independently selected from —CH$_2$—NH—, —CH$_2$—S—, —CH$_2$—CH$_2$—, —CH$_2$—O— and CH$_7$—CO—.

Preferred compounds of formula (III) include H-Tyr-Arg-Leu-Arg-Tyr-Tyr-Arg-Leu-Arg-Tyr-NH$_2$ (SEQ. ID. NO. 9) or H-Tyr-Arg-Leu-Arg-Tyr-Tyr-Arg-Leu-Arg-Tyr-Tyr-Arg-Leu-ArgTyr-NH$_2$ (SEQ. ID. NO. 10).

In another aspect, NPY Y$_4$ receptor agonists, such as those of formulas (I-III), are mixed or combined with NPY Y$_2$ receptor agonists, such as analogs of PYY(25-36) or PYY(22-36), for controlling an NPY mediated physiological response in a subject, e.g. to suppress appetite, such analogs of PYY(25-36) and of P(22-36), respectively, having formulas (IV) and (V) below:

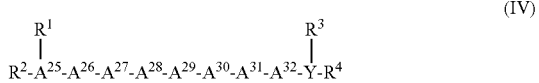

(IV)

wherein:
the N-terminal amino acid is bonded to R$^1$ and R$^2$;
Y is a chain of 0-4 amino acids, inclusive, where the C-terminal amino acid has a carboxylamide group; which is independently bonded to R$^3$ and R$^4$, e.g.,

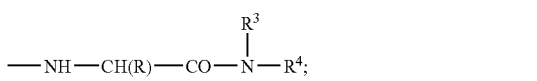

R$^1$ and R$^2$ are each independently bonded to the amino group of the N-terminal amino acid and selected from H, (C$_1$-C$_{12}$)alkyl, (C$_6$-C$_{18}$)acyl, (C$_1$-C$_{12}$)acyl, (C$_7$-C$_{18}$) aralkyl, and (C$_7$-C$_{18}$)alkaryl;
R$^3$ and R$^4$ are each independently bonded to the amide group of the C-terminus amino acid, e.g.,

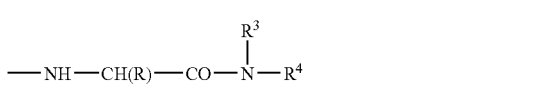

(where R denotes the side chain group of the amino acid, e.g. R=H in Gly, etc.), and selected from H, (C$_1$-C$_{12}$) alkyl (e.g. methyl), (C$_6$-C$_{18}$)aryl (e.g. phenyl), (C$_1$-C$_{12}$) acyl (formyl, acetyl, napthateneacetyl, and myristoyl), (C$_7$-C$_{18}$) aralkyl (e.g. benzyl), and (C$_7$-C$_{18}$)alkaryl (e.g. p-methlyphenyl);
A$^{25}$ is Arg, Lys, homo-Arg, diethyl-homo-Arg, lys-ε-NH—R where R is H, a branched or straight chain (C$_1$-C$_{10}$) alkyl group, or an aryl group, Orn or is deleted;
A$^{26}$ is Ala, His, Thr, 3-Me-His, 1-Me-His, β-pyrozolyiaianin, N-Me-His, Arg, Lys, homo-Arg, diethyl-homo-Arg, Lys-e-NH—R where R is H, a branched or straight chain (C$_1$-C$_{10}$) alkyl group, or an aryl group, Orn or is deleted;
A$^{27}$ is an aromatic amino acid;
A$^{28}$ is Leu, Ile, Val, Tip Nle, Nva, Aib, Anb, or N-Me-Leu;
A$^{29}$ is Asn, Ala, Gln, Fly, Trp, or N-Me-Asn;
A$^{30}$ is Leu, Ile, Val, Trp, Nle, Nva, Aib, Anb, or N-Me-Leu;
A$^{31}$ is Val, Ile, Trp, Nva, Aib, Anb, or N-Me-Val;
A$^{32}$ is Thr, Ser, N-Me-Ser, N-Me-Thr, or D-Trp; and
wherein the compound optionally includes one or two pseudopeptide bonds where each pseudopeptide bond is independently selected from —CH$_2$—NH—, —CH$_2$—S—, —CH$_2$—CH$_2$—, —CH$_2$—O— and C$_2$—CO—;

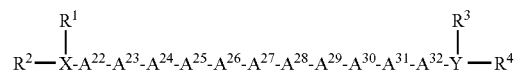

(V)

wherein
X is a chain of 0-5 amino acids, inclusive, where the N-terminal amino acid is bonded to R$^1$ and R$^2$ by the nitrogen of the amino group of the N-terminal amino acid;
Y is a chain of 0-4 amino acids, inclusive, where the C-terminal amino acid has a carboxylamide group; which is independently bonded to R$^3$ and R$^4$, e.g.,

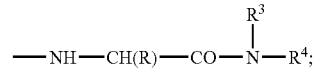

R$^1$ and R$^2$ are each independently bonded to the amino group of the N-terminal amino acid and selected from H, (C$_1$-C$_{12}$)alkyl, (C$_6$-C$_{18}$)aryl, (C$_1$-C$_{12}$)acyl, (C$_7$-C$_{18}$) aralkyl, and (C$_7$-C$_{18}$)alkaryl;
R$^3$ and R$^4$ are each independently bonded to the amide group of the C-terminus amino acid, e.g.,

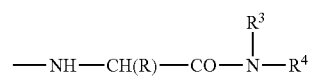

(where R denotes the side chain group of the amino acid, e.g. R=H in Gly, etc.), and selected from H, (C$_1$-C$_{12}$) alkyl (e.g. methyl), (C$_6$-C$_{18}$)aryl (e.g. phenyl), (C$_1$-C$_{12}$) acyl (formyl, acetyl, napthaleneacetyl, and myristoyl), (C$_7$-C$_{18}$)aralkyl (e.g. benzyl), and (C$_7$-C$_{18}$)alkaryl (e.g. p-methlyphenyl);
A$^{22}$ is an aromatic amino acid, Ala, Aib, Anb, N-Me-Ala or is deleted;
A$^{23}$ is Ser, Thr, Ala, Aib, N-Me-Ser, N-Me-Thr, N-Me-Ala or is deleted;
A$^{24}$ is Leu, Ile, Nle, Val, Trp, Gly, Nva, Aib, Anb, N-Me-Leu or is deleted;
A$^{25}$ is Arg, Lys, homo-Arg, diethyl-homo-Arg, Lys-pε-NH—R (where R is H, a branched or straight chain (C$_1$-C$_{10}$) alkyl group, or an aryl group), Orn or is delete;

A²⁶ is Ala, His, Thr, 3-Me-His, 1-Me-His, β-pyrazolylalaline, N-Me-His, Arg, Lys, homo-Arg, diethyl-homo-Arg, Lys-F—NH—R (where R is H, a branched or straight chain (C₁-C₁₀) alkyl group, an aryl group, or a pharmaceutically acceptable salt thereof), Orn or is deleted;

A²⁷ is an aromatic amino acid;

A is Leu, Ile, Nle, Val, Trp, Aib, Anb or N-Me-Leu;

A²⁹ is Asn, Ala, Gln, Gly, Trp or N-Me-Asn;

A³⁰ is Leu, Ile, Nle, Nva, Fla, Val, Trp, Aib, Anb or N-Me-Leu;

A³¹ is Val, Len, Nle, Nva, Ile, Trp, Aib, Anb or N-Me-Val;

A³² is Thr; Ser, D-Trp, N-Me-Ser or N-Me-Thr; and wherein the compound optionally includes one or two pseudopeptide bonds where each pseudopeptide bond is independently selected from —CH₂—NH—, —CH₂—S—, —CH₂—CH₂—, CH₂—O— and CH₂—CO—.

A preferred compound of formula (IV) includes N-α-Ac [Trp²⁷, ψ³⁵ᐟ³⁶]PYY(25-36)-NH₂ (SEQ. ID. NO. 5), referred to as BT-56, N-α-Ac[Trp³⁰]PYY(25-36)-NH₂ (SEQ. ID. NO. 4), referred to as BWX-15, and N-α-Ac-[Trp³⁰,ψ³⁵ᐟ³⁶]PYY (25-36)-NH₂ (SEQ. ID. NO. 6), referred to as BT-123, wherein N in the foregoing formulas is —CH2-NH—. A preferred compound of formula (V) includes N-α-Ac [Nle²⁴ᐟ²⁸,Trp³⁰,Nva³¹,ψ³⁵ᐟ³⁶]PYY(22-36)-NH₂ (SEQ. ID. NO. 7) referred to as B-48, wherein NV is —CH2-NH—.

The formulas of I-V, as indicated above, optionally include at least one pseudopeptide bond between amino acid residues, By "psuedopeptide bond" is meant that the carbon atom participating in the bond between two residues is reduced from a carbonyl carbon to a methylene carbon, i.e., CH₂—NH; or less preferably that of CO—NH is replaced with any of CH₂—S, CH₂—CH₂, CH₂—O, or CH₂—CO. A psuedopeptide bond may be symbolized herein by "ψ". The psuedopeptide bond analogs can be used to form dimeric analogs. A detailed discussion of psuedopeptide bonds is given in Coy et al. (1998) *Tetrahedon* 44:835-841.

In another aspect, the invention features a method of controlling the food intake, i.e. appetite, of a subject comprising administering to said subject the compound of formula I, II, or III alone or in combination with formulas IV or V.

In other preferred embodiments, a therapeutically effective amount of a compound of formula I, II, or III alone, or in combination with formulas IV or V, and a pharmaceutically acceptable carrier substance together form a therapeutic composition capable of suppressing an NPY mediated physiological response.

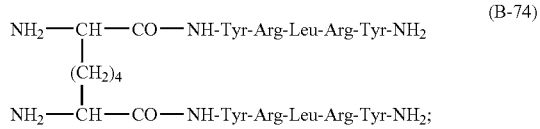

Figure 2:
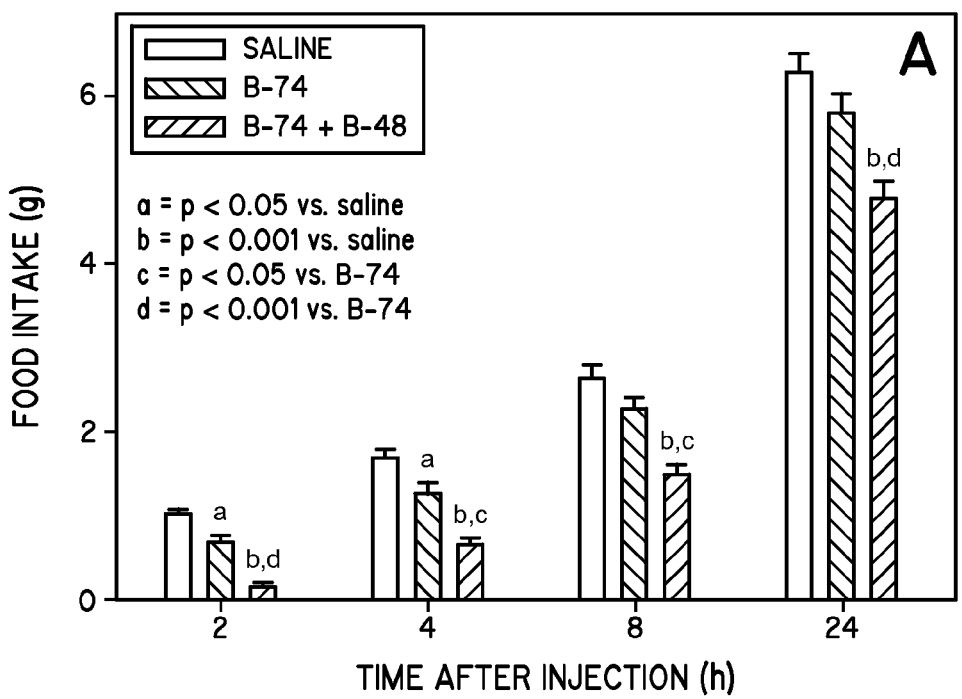
Figure 3:
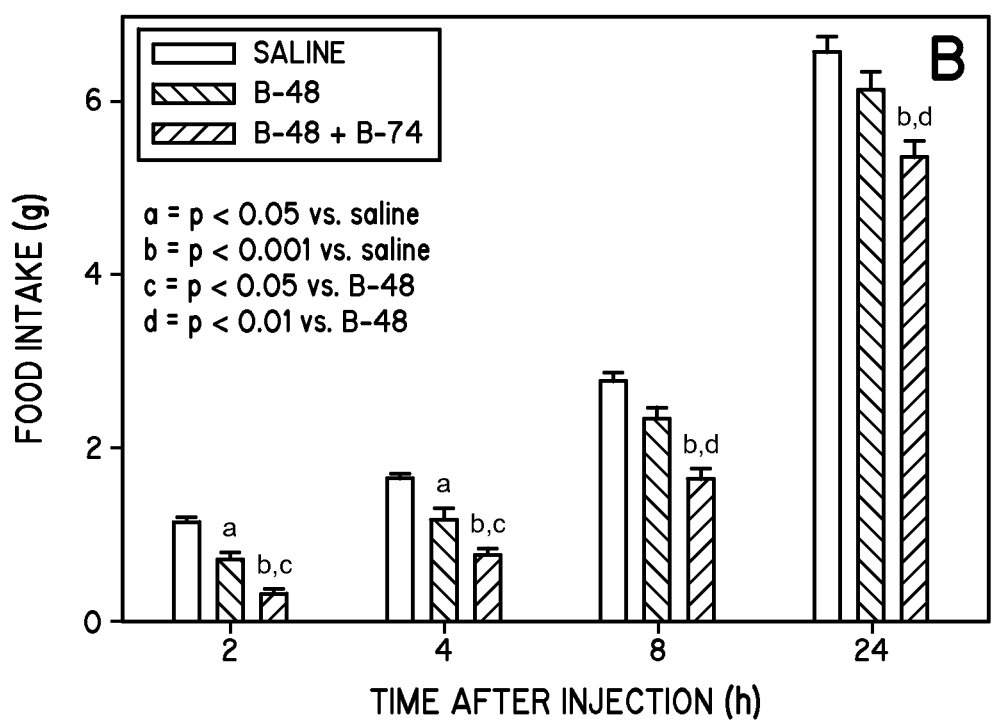

FIG. 2 is a graph representing the feeding patterns of animals treated with a PP(32-36) analog (Y4 receptor agonist), and a mixture of the PP(32-36) analog and a PYY(22-36) analog (Y2 receptor agonist), by intraperitoneal injection. The compounds tested include a control (saline),

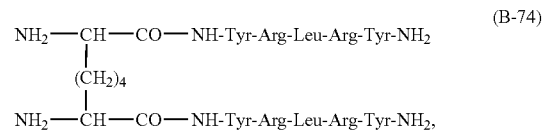

and a combination of B-74 and N-α-Ac[Nle²⁴ᐟ²⁸,Trp³⁰, Nva³¹,ψ³⁵ᐟ³⁶]PYY(22-36)-NH₂ (SEQ. ID. NO 7) (B-48) wherein ψ is —CH2-NH—; and FIG. 3 is a graph representing the feeding patterns of animals treated with a PYY(22-36) analog (Y2 agonist receptor), and a mixture of the PYY(22-36) analog and a PP(32-36) analog (Y4 receptor agonist), by intraperitoneal injection. The compounds tested include a control (saline), N-α-Ac [Nle²⁴ᐟ²⁸,Trp³⁰,Nva³¹, ψ³⁵ᐟ³⁶]PYY(22-36)-NH₂ (SEQ. ID. NO. 7) (B-48) wherein ψ is —CH₂—NH—, and a combination of B-48 and

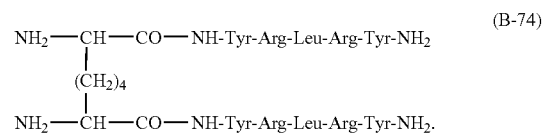

DETAILED DESCRIPTION OF THE INVENTION

The present invention is directed to neuropeptide Y ("NPY") Y₄ receptor agonists including pancreatic polypeptide (PP), analogs thereof, and peptide fragments of PP, e.g. PP(32-36), and analogs thereof, to pharmaceutical compositions containing such Y₄ receptor agonists, and to methods for treatment of mammals using the same. The NPY Y₄ receptor agonists may be administered to mammals either alone or in combination with NPY Y, receptor agonists including peptide YY (PYY) (3-36), analogs thereof, and to peptide fragments of P (3-36), e.g. PYY(22-36) and PYY(25-36), and analogs thereof, such as to control food intake in mammals, blood pressure, cardiovascular response, libido, circadian rhythm, hyperlipidimia, chronic pancreatitis, and nonalcoholic fatty liver disease including nonalcoholic steatohepatitis.

one advantage of using the Y4 selective ligands of the present invention is that they can suppress food intake on peripheral administration, whereas Y1 and Y5 selective ligands, as described above, have to penetrate the BBB to modulate food intake. Additionally, an advantage of using Y2 selective ligands is that they also can suppress the food intake oil peripheral administration. Therefore, the inventor has developed NPY Y₄ receptor agonists that can be used alone or mixed with NPY Y₂ receptor agonists, as are disclosed in U.S. Pat. Nos. 5,604,203, and 6,046,167 to Balasubramaniam, which are herein incorporated by reference, for controlling an NPY mediated physiological response in a subject, such as to control food intake in mammals by suppressing appetite.

Accordingly, in one aspect, the present invention features NPY Y₄ receptor agonists of PP(32-36) and analogs thereof, such pentapeptide analogs having the formula:

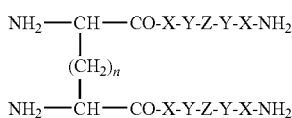
 (I)

wherein:
each X, independently, is an aromatic amino acid;
each Y, independently, is an amino acid having a guanidino group;
each Z, independently, is an aliphatic amino acid;
n=1, 2, 3 or 4; and
wherein the compound optionally includes one or two pseudopeptide bonds where each pseudopeptide bond is independently selected from —CH—NH—, —CH$_2$—S—, —CH$_2$—C$_2$—, —CH$_2$—O— and CH$_2$—CO—.

A preferred compound of formula (I) includes,

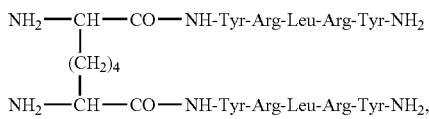

(which is referred to as B-74).

In another aspect, the present invention features NPY Y$_4$ receptor agonists or pentapeptide analogs of PP(32-36) having the formula:

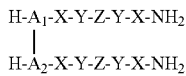

wherein:
each X, independently, is an aromatic amino acid;
each Y, independently, is an amino acid having a guanidino group;
each Z, independently, is an aliphatic amino acid;
A1 and A2, independently, are selected from Cys, Pen, Glu, Asp, Lys, and Dpr; and
wherein the compound optionally includes one or two pseudopeptide bonds where each pseudopeptide bond is independently selected from —CH$_2$—NH—, —CH$_2$—S—, —CH$_2$—CH$_2$—, —CH$_2$—O— and CH$_2$—CO—.

A preferred compound of formula (II) includes,

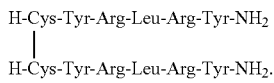

In another aspect, the present invention features NPY Y$_4$ receptor agonists or pentapeptide analogs of PP(32-36) having the formula:

H—[X—Y—Z—Y—X]$_n$—NH$_2$    (III)

wherein:
each X, independently, is an aromatic amino acid;
each Y, independently, is an amino acid having a guanidino group;
each Z, independently, is an aliphatic amino acid;
n=1, 2, 3 or 4; and
wherein the compound optionally includes one or two pseudopeptide bonds where each pseudopeptide bond is independently selected from CH$_2$—NH—, —CH$_2$—S—, —CH$_2$—CH$_2$—, —CH$_2$—O— and CH$_2$—CO—.

Preferred compounds of formula (II) include H-Tyr-Arg-Leu-Arg-Tyr-Tyr-Arg-Leu-Arg-Tyr-NH$_2$ (SEQ. ID. NO. 9) or H-Tyr-Arg-Leu-Arg-Tyr-Tyr-Arg-Leu-Arg-Tyr-Tyr-Arg-Leu-Arg-Tyr-NH$_2$ (SEQ. ID. NO. 10).

For formulas I-III, aromatic amino acids can include, for example, phenylalanine, tryptophan, or tyrosine, which is a hydroxyl aromatic amino acid; aliphatic amino acids can include, for example, isoleucine, leucine, norvaline, glycine, alanine, or valine; and amino acids that have a guanidino group may include, for example, arginine. In addition, the C-terminal of the compounds of formulas (I-III) are amidated.

In another aspect, NPY Y$_4$ receptor agonists, such as those of formulas (I-III), are mixed or combined with NPY Y$_2$ receptor agonists, such as analogs of PYY(25-36), for controlling an NPY mediated physiological response in a subject, e.g. to suppress appetite, such analogs of PYY(25-36) having the formula:

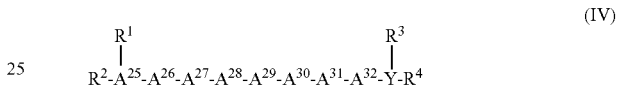
 (IV)

wherein:
the N-terminal amino acid is bonded to R$^1$ and R$^2$;
Y is a chain of 0-4 amino acids, inclusive, where the C-terminal amino acid has a carboxyl amide group; which is independently bonded to R$^3$ and R$^4$, e.g.,

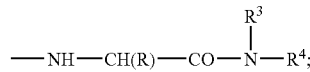

R$^1$ and R$^2$ are each independently bonded to the amino group of the N-terminal amino acid and selected from H, (C$_1$-C$_{12}$)alkyl (e.g. methyl), (C$_6$-C$_{18}$)aryl (e.g. phenyl), (C$_1$-C$_{12}$)acyl (formyl, acetyl, napthaleneacetyl, and myristoyl), (C$_7$-C$_{18}$)aralkyl (e.g. benzyl), and (C$_7$-C$_{18}$)alkaryl (e.g. p-methlyphenyl);
R$^3$ and R$^4$ are each independently bonded to the amide group of the C-terminus amino acid, e.g.,

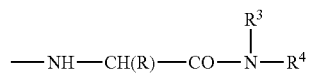

(where R denotes the side chain group of the amino acid, e.g. R=H in Gly, etc.), and selected from H, (C$_1$-C$_{12}$) alkyl (e.g. methyl), (C$_6$-C$_{18}$)aryl (e.g. phenyl), (C$_1$-C$_{12}$) acyl (formyl, acetyl, napthaleneacetyl, and myristoyl), (C$_7$-C$_{18}$)aralkyl (e.g. benzyl), and (C$_7$-C$_{18}$)alkaryl (e.g. p-methlyphenyl);
A$^{25}$ is Arg, Lys, homo-Arg, diethyl-homo-Arg, lys-ε-NH—R (where R is H, a branched or straight chain (C$_1$-C$_{10}$) alkyl group, or an aryl group), Orn or is deleted;
A$^{26}$ is Ala, His, Thr, 3-Me-His, 1-Me-His, β-pyrozolylalanin, N-Me-His, Arg, Lys, homo-Arg, diethyl-homo-Arg, Lys-ε-NH—R (where R is H, a branched or straight chain (C$_1$-C$_{10}$) alkyl group, or an aryl group), Orn or is deleted;
A$^{27}$ is an aromatic amino acid:
A$^{28}$ is Leu, Ile, Val, Trp Nle, Nva, Aib, Anb, or N-Me-Leu;

$A^{29}$ is Asn, Ala, Gln, Fly, Trp, or N-Me-Asn;
$A^{30}$ is Leu, Ile, Val, Trp, Nle, Nva, Aib, Anb, or N-Me-Leu;
$A^{31}$ is Val, Ile, Trp, Nva, Aib, Anb, or N-Me-Val;
$A^{32}$ is Thr, Ser N-Me-Ser, N-Me-Thr, or D-Trp.

In preferred embodiments Y is $A^{33}$-$A^{34}$-$A^{35}$-$A^{36}$ wherein
$A^{33}$ is Arg, Lys, homo-Arg, diethyl-homo-Arg, Lys-F—NH—R (where R is H, a branched or straight chain ($C_1$-$C_{10}$) alkyl group, or ($C_6$-$C_{18}$) aryl group), Cys, or Orn
$A^{34}$ is Gln, Asn, Ala, Gly, N-Me-Gln, Aib, Cys, or Anb;
$A^{35}$ is Arg, Lys, homo-Arg, diethyl-homo-Arg, Lys-ε-NH—R (where R is H, a branched or straight chain ($C_1$-$C_{10}$) alkyl group, or ($C_6$-$C_{18}$) aryl group), Cys, or Orn; and
$A^{36}$ is an aromatic amino acid, Cys, or a pharmaceutically acceptable salt thereof.

Most preferably, the compound of formula (IV) includes N-α-Ac[$Trp^{27}$, $\psi^{35/36}$]PYY(25-36)-$NH_2$ (SEQ. ID. NO. 5), referred to as BT-56, and N-α-Ac[$Trp^3$]PYY(25-36)-$NH_2$ (SEQ. ID. NO. 4), referred to as BWX-115, and N-α-Ac-[$Trp^{30}$,$\psi^{35/36}$]PYY(25-36)-$NH_2$ (SEQ. ID. NO. 6), referred to as BT-1123, wherein y in the foregoing formulas is —CH2-NH—.

In yet another aspect, NPY $Y_4$ receptor agonists, such as those of formulas (I-III), are mixed with NPY $Y_2$ receptor agonists, such as analogs of PYY(22-36), for controlling an NPY mediated physiological response in a subject, e.g. to suppress appetite, such analogs of PYY(22-36) having the formula:

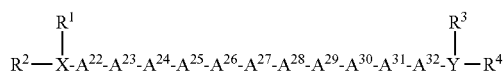

(V)

wherein
X is a chain of 0-5 amino acids, inclusive, where the N-terminal amino acid is bonded to $R^1$ and R2 by the nitrogen of the amino group of the N-terminal amino acid;
Y is a chain of 0-4 amino acids, inclusive, where the C-terminal amino acid has a carboxylamide group; which is independently bonded to $R^3$ and $R^4$, e.g.,

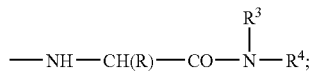

$R^1$ and $R^2$ are each independently bonded to the amino group of the N-terminal amino acid and selected from H, ($C_1$-$C_{12}$)alkyl (e.g. methyl), ($C_6$-$C_{18}$)aryl (e.g. phenyl), ($C_1$-$C_{12}$)acyl (formyl, acetyl, napthaleneacetyl, and myristoyl), ($C_7$-$C_{18}$)aralkyl (e.g. benzyl), and ($C_7$-$C_{18}$)alkaryl (e.g. p-methlyphenyl);
$R^3$ and $R^4$ are each independently bonded to the amide group of the C-terminal amino acid, e.g.,

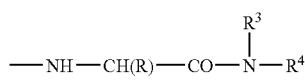

(where R denotes the side chain group of the amino acid, e.g. R=H in Gly, etc.), and selected from H, ($C_1$-$C_{12}$) alkyl (e.g. methyl), ($C_6$-$C_{18}$)aryl (e.g. phenyl), ($C_1$-$C_{12}$) acyl (formyl, acetyl, napthaleneacetyl, and myristoyl), ($C_7$-$C_{18}$)aralkyl (e.g. benzyl), and ($C_7$-$C_{18}$)alkaryl (e.g. p-methlyphenyl);

$A^{22}$ is an aromatic amino acid, Ala, Aib, Anb, N-Me-Ala or is deleted;
$A^{23}$ is Ser, Thr, Ala, Aib, N-Me-Ser, N-Me-Thr, N-Me-Ala or is deleted;
$A^{24}$ is Leu, Ile, Nle, Val, Trp, Gly, Nva, Aib, Anb, N-Me-Leu or is deleted;
$A^{25}$ is Arg, Lys, homo-Arg, diethyl-homo-Arg, Lys-pε-NH—R (where R is H, a branched or straight chain ($C_1$-$C_{10}$) alkyl group, or an aryl group), Orn or is deleted;
$A^{26}$ is Ala, His, Thr, 3-Me-His, 1-Me-His, β-pyrazolylalaline, N-Me-His, Arg, Lys, homo-Arg, diethyl-homo-Arg, Lys-ε-NH—R (where R is H, a branched or straight chain ($C_1$-$C_{10}$) alkyl group, an aryl group, or a pharmaceutically acceptable salt thereof), Orn or is deleted;
$A^{27}$ is an aromatic amino acid;
$A^{28}$ is Leu, Ile, Nle, Val, Trp, Aib, Anb or N-Me-Leu;
$A^{29}$ is Asn, Ala, Gln, Gly, Trp or N-Me-Asn;
$A^{30}$ is Leu, Ile, Nle, Nva, Fla, Val, Trp, Aib, Anb or N-Me-Leu;
$A^{31}$ is Val, Leu, Nle, Nva, Ile, Trp, Aib, Anb or N-Me-Val; and
$A^{32}$ is Thr, Ser, D-Trp, N-Me-Ser or N-Me-Thr.

In preferred embodiments, Y is $A^{33}$-$A^{34}$-$A^{35}$-$A^{36}$ wherein
$A^{33}$ is Arg, Lys, homo-Arg, diethyl-homo-Arg, Lys-ε-N—HR (where R is U, a branched or straight chain ($C_1$-$C_{10}$) alkyl group, or an aryl group), Cys, or Orn
$A^{34}$ is Cys, Gln, Asn, Ala, Gly, N-Me-Gln, Aib, or Anb;
$A^{35}$ is Arg, Lys, homo-Arg, diethyl-homo-Arg, Lys-ε-NH—R (where R is U, a branched or straight chain ($C_1$-$C_{10}$) alkyl group, or an aryl group), Cys, or Orn; and
$A^{36}$ is an aromatic amino acid, Cys, or a pharmaceutically acceptable salt thereof.

Most preferably, the compound of formula (V) includes N-α-Ac[$Nle^{24,25}$,$Trp^{30}$,$Nva^{31}$,$\psi^{35/36}$]PYY(22-36)-NH, (SEQ. ID. NO. 7) referred to as B-48, wherein ψ is —CH2NH—.

Concerning formulas IV and V, reference to the ($C_1$-$C_{12}$) acyl for R1 and R2 can include an aliphatic acyl (e.g. $CH_3CO$) or an aromatic acyl (e.g. $C_6H_5CO$).

Additionally, the formulas of I-V optionally include at least one pseudopeptide bond between amino acids residues. By "psuedopeptide bond" is meant that the carbon atom participating in the bond between two residues is reduced from a carbonyl carbon to a methylene carbon, i.e., CH2-NH; or less preferably that of CO—NH is replaced with any of $CH_2$—S, $CH_2$—$CH_2$, $CH_2$—O, or $CH_2$—CO. A psuedopeptide pseudopeptide bond is symbolized herein by "ψ". Preferably, the psuedopeptide bonds are located between one or more amino acid residues. In addition, such psuedopeptide bond analogs can be used to form dimeric analogs. A detailed discussion of psuedopeptide bonds is given in Coy et al., (1998) *Tetrahedon* 44:835-841.

Accordingly, in another aspect and as already specifically illustrated by certain of the preferred compounds, the invention features dimers, trimers, etc. of compounds having the formula (I-V). These dimers, trimers, etc. may be prepared, for example, by dimerizing compounds of formula (I-V) with dicarboxylic acids (e.g., succinic acid), cystine, or diaminodicarboxylic acid (e.g., 2,6-diaminopimelic acid) as is known in the art. Resulting compounds can include, for example, pentapeptide linear tandem or parallel dimers.

In another aspect, the invention features a method of controlling the food intake, i.e. appetite, of a subject comprising administering to said subject the compound of formula I, II, or III alone or in combination with formulas IV or V. These compounds also can be conjugated to carriers, such carriers can include albumin, such as cationized albumin (Endocrinology 126:977-984 (1990); J. Pharmacol Exp. Therao. 268:

791-796 (1994)), polyethylene glycol, polyglutamic acid, polyleucine, polyisoleucine or polylysine, e.g., MAP.

In other preferred embodiments, a therapeutically effective amount of a compound of formula I, II, or III alone, or in combination with formulas IV or V, and a pharmaceutically acceptable carrier substance, e.g., magnesium carbonate or lactose, together form a therapeutic composition capable of suppressing an NPY mediated physiological response. This composition call be in the form of a pill, tablet, capsule, liquid, or sustained released tablet for oral administration; or a liquid for nasal administration as drops or spray; or a liquid for intravenous, subcutaneous, parenteral, or intraperitoneal administration. Another preferred form for administration includes a biodegradable sustained-release composition for intramuscular administration to a subject in need of the composition. Preferably, the composition includes a lipophilic salt and is suitable for administration in the form of an oil emulsion or dispersion to a subject in need of the composition.

In yet another aspect, the invention features methods for controlling an NPY mediated physiological response in a subject; such methods involve administering a compound of formula I, II, or III alone, or in combination with formulas IV or V, to a subject in a dosage effective to control blood pressure, cardiovascular response, libido, circadian rhythm, hyperlipidimia, chronic pancreatitis, and nonalcoholic fatty liver disease including nonalcoholic steatohepatitis.

The NPY $Y_4$ receptor agonists including pancreatic polypeptide (PP), analogs thereof, and peptide fragments of PP, e.g. PP(32-36), and analogs thereof such as those of compounds (I-III), either alone or in combination with NPY $Y_2$ receptor agonists including peptide YY (PYY) (3-36), analogs thereof, and to peptide fragments of PYY(3-36), e.g. PYY(22-36) and PYY(25-36), and analogs thereof such as those of compounds (IV-V), also can be useful in treating any number of illnesses that involve eating disorders, cardiovascular function, alterations in sexual function, as well as disorders of sleep and circadian rhythms (see, e.g., *Harrison's Principles of Internal Medicine*, McGraw-Hill Inc., New York, 12th ed.).

Other features and advantages of the invention will be apparent to one skilled in the art.

The symbol A1, A2, A3, and the like; and Tyr, Lys or the like, as found in a peptide sequence herein stands for an amino acid residue, e.g., —N—CH(R)—CO— when it is at the N-terminus, or —NH—CH(R)—CO— when it is at any other position, where R denotes the side chain (or identifying group) of an amino acid or its residue. For example, R is $CH_2COOH$ for Asp, R is —H for Gly, R is —$CH_2OH$ for Ser, R is —$CH_3$ for Ala and R is —$CH_2CH_2CH_2CH_2NH_2$ for Lys.

As set forth above and for convenience in describing this invention, the conventional and certain unconventional abbreviations for the various amino acids are used. They are familiar to those skilled in the art; but for clarity are listed below, All peptide sequences mentioned herein are written according to the usual convention whereby the N terminal amino acid is on the left and the C-terminal amino acid is on the right. A short line between two amino acid residues indicates a peptide bond.

ABBREVIATIONS

Common

Asp=D Aspartic Acid
Ala=A=Alanine
Arg=R=Arginine
Asn=N=Asparagine
Cys=C=Cysteine
Gly=G=Glycine
Glu=E=Glutamic Acid
Gln Q=Glutamine
His=H=Histidine
Ile=I=Isoleucine
Leu=L=Leucine
Lys=K=Lysine
Met=M=Methionine
Phe=F=Phenylalanine
Pro=P=Proline
Ser=S=Serine
Thr=T=Threonine
Trp=W=Tryptophan
Tyr=Y=Tyrosine
Val=V=Valine.

Abbreviations (uncommon).
Aoc=8-aminooctanoic acid
Orn=Ornithine
Nal=2-napthylalanine
Thi=2-thienylalanine
Pcp=4-chlorophenylalanine
Bth=3-benzothienyalanine
Bip=4,4'-biphenylalanine
Tic=tetrahydroisoquinoline-3-carboxylic acid
Aib=aminoisobutyric acid
Anb=alpha-aminonornalbutyric acid
$Ac_6c$=1-aminocyclohexanecarboxylic acid
D-Pal=beta-(3-pyridyl)alanine;
Tcc=tetrahydrocarbolcnecarboxylic acid
Abu=α-aminonormalbutyric acid
$hArg(Pr)_2$=N,N'-guanidino-(dipropyl)-homoaxginirne
Tic-OH=1,2,3,4 tetrahydroisoquinoline-7-hydroxy-3-carboxylic acid
Dip=3,3-diphenylalanine
2-Nal=3(2-naphthylalanine)
Tfp=Paratrifluoromethyl phenylalanine
Fla=3-(9-Fluorenyl)alanine
Flg=9-Fluorenylglycine
Cit=Citruline
Adp=2,5-diaminoadipic acid
Pim=2,6-diaminopimelic acid
Sub=2,7-diaminosuberic acid
Nle=Norleucine
Nva=Norvaline
Thz=4-Thiazolylalanine
Dpr=Dap=2,3-diaminopropionic acid
Pyr=Pyroglutamic acid
Tip=1,2,3,4-tetrahydronorharman-3-carboxylic acid
Pen=Penicillamine.
Other Abbreviations:
Fmoc=N-(9-fluorenyl)methoxycarbonyl.

The terms "C2-C4-alkenyl" and "C2-C6-alkenyl" as used herein refer to a 2 to 4 to 6 straight- or branched-chain of carbon atoms which contains a carbon-carbon double bond, such as allyl, propenyl, butanol, isoprenyl and the like.

The terms "C1-C18-alkyl" as used herein refer to straight or branched chain alkyl radicals having from 1 to 18 carbon atoms including, but not limited to, methyl, ethyl, propyl, isopropyl, butyl, isobutyl, sec-butyl, pentyl, neopentyl hexyl, and the like.

The term "C6-C18-aryl" as used herein refers to phenyl or to a "bicyclic carbocyclic" group or "bicyclic carbocycle" having two fused carbocyclic rings, each ring having 5, 6 or 7 carbon atoms, and each ring being fully saturated, partially saturated or aromatic. Bicyclic carbocyclic groups include, but are not limited to, naphthyl, tetrahydronaphthyl, decalin, indanyl, indenyl and the like.

The term "C7-C18-arylalkyl" as used herein refers to an aryl group appended to a C1-C4-alkyl radical including, but not limited to, benzyl, phenethyl, naphthylmethyl and the like.

The term "bicyclic heterocycle" as used herein refers to a group having two fused rings, one or both of which are heterocyclic rings as defined herein. When both rings are not heterocyclic, the other ring is carbocyclic and is saturated, partially saturated or aromatic, preferably a benzene ring. Bicyclic heterocyclic groups can be unsubstituted or monosubstituted or disubstituted with substituents independently selected from hydroxy, halo, oxo (=O), amino, C1-C4-alkylamino, di-(C1-C4)-alkylamino, C1-C4-alkoxy, thio-C1-C4-alkoxy, carboxy, C1-C4-alkoxycarbonyl, C1-C4-alkyl, C3-C8-cycloalkyl, —OSO$_3$H and halo-C1-C4-alkyl. Examples of bicyclic heterocycles include indole, 5-hydroxyindole, quinoline, isoquinoline, tetrahydroisoquinoline, quinoxaline, benzimidazole, benzofuran, and the like.

The term "cyclo-C3-C10-alkyl" as used herein refers to an aliphatic monocyclic of 3 to 10 or bicyclic group having 6 to 10 carbon atoms including, but not limited to, cyclopropyl, cyclobutyl, cyclopentyl, cyclohexyl, cyclooctyl, adamantyl, and the like.

The term "halo" or "halogen" as used herein refers to chloro, bromo, iodo or fluoro.

The term "halo-C1-C4-alkyl" as used herein refers to a lower alkyl radical in which one to three hydrogen atoms have been replaced by a halogen including, but not limited to, chloromethyl, 2-fluoroethyl, trifluoromethyl and the like.

The term "monocyclic heterocyclic group" or "monocyclic heterocycle" as used herein refers to any 3- or 4-membered ring containing a heteroatom selected from oxygen, nitrogen and sulfur, or a 5- or 6-membered ring containing carbon atoms and one, two or three nitrogen atoms; one nitrogen and one sulfur atom; or one nitrogen and one oxygen atom; wherein the 5-membered ring has 0-2 double bonds and the 6-membered ring has 0-3 double bonds; wherein the nitrogen and sulfur heteroatoms may optionally be oxidized; and wherein the nitrogen heteroatom may optionally be quaternized. Heterocycles include, but are not limited to, pyridyl, imidazolyl, furyl, thienyl, pyrazinyl, pyrrolyl, pyrimidyl and the like. Heterocyclics may be unsubstituted or mono- or disubstituted with substituents independently selected from hydroxy, halo, oxo (=O), amino, C1-C4-alkylamino, (C1-C4)2-alkylamino, C1-C4-alkoxy, thio-C1-C4-alkoxy, carboxy, C1-C4-alkoxycarbonyl, C1-C4-alkyl, C3-C8-cycloalkyl, —OSO$_3$H and halo-C1-C4-alkyl.

The term "peptide bond" as used herein refers to the chemical bond between carbon and nitrogen in the bivalent group CONH that unites amino acid residues in a peptide.

In addition, the above compounds may contain two or more asymmetric carbon atoms and thus can exist as pure diastereomers, mixtures of diastereomers, diastereomeric racemates or mixtures of diastereomeric racemates. As such, the present invention includes within its scope all of the isomeric forms. In keeping with standard peptide nomenclature, J. Biol. Chem., 1969, 243:3557-59, abbreviations for amino acid residues are used herein.

It is noted that all amino acid residue sequences are represented herein by formulae whose left to right orientation is in the conventional direction of amino-terminus to carboxy-terminus.

Administration

The amount of active ingredient that may be combined with the carrier materials to produce a single dosage form will vary depending upon the host treated, the particular treatment and the particular mode of administration.

It will be understood, however, that the specific dose level for any particular patient will depend upon a variety of factors including the activity of the specific compound employed, the age, body weight general health, sex, diet, time of administration, rate of excretion, drug combination, and the severity of the particular disease undergoing therapy.

However, generally speaking the following guidelines will suffice When an NPY $Y_4$ receptor agonist, such as those of compounds (I-III), is either used alone or in combination with an NPY $Y_2$ receptor agonist, such as those of compounds (IV-V), as an agonist(s) of NPY in a human subject, the total daily dose administered in single or divided doses may be in amounts, for example, from 0.001 to 1000 mg a day and more usually 1 to 1000 mg. Dosage unit compositions may contain such amounts of submultiples thereof to make up the daily dose.

The compounds useful in the present inventive method may be administered by any suitable means. One skilled in the art will appreciate that many suitable methods of administering the compounds to an animal in the context of the present invention, in particular a human, are available, and, although more than one route may be used to administer a particular compounds, a particular route of administration may provide a more immediate and more effective reaction than another route.

The compositions according to the present invention may be formulated for administration by any suitable route such as the oral, rectal, nasal, topical (dermal) or parenteral administration route. Thus, the composition may be in the form of tablets, capsules, suspensions, emulsions, solutions, injectables, suppositories, sprays, aerosols and in other suitable form.

Formulations for oral use include tablets that contain the active ingredient in admixture with non-toxic pharmaceutically acceptable excipients. These excipients may be, for example, inert diluents, such as calcium carbonate, sodium chloride, lactose, calcium phosphate or sodium phosphate; granulating and disintegrating agents, for example, potato starch or alginic acid; binding agents, for example, starch, gelatin or acacia; and lubricating agents, for example, magnesium stearate, stearic acid or talc. Other pharmaceutically acceptable excipients can be colorants, flavoring agents, plasticizers, humectants etc. The tablets may be uncoated or they may be coated by known techniques, optionally to delay disintegration and absorption in the gastrointestinal tract and thereby provide a sustained action over a longer period. For example, a time delay material such as glyceryl monostearate or glyceryl distearate may be employed.

Formulations for oral use may also be presented as chewing tablets, or as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin, or olive oil.

Powders, dispersible powders or granules suitable for preparation of an aqueous suspension by addition of water are also convenient dosage forms of the present invention. Formulation as a suspension provide the active ingredient in admixture with a dispersing or wetting agent, suspending agent and one or more preservatives. Suitable dispersing or wetting agents are, for example, naturally-occurring phosphatides, as e.g. lecithin, or condensation products of ethylene oxide with e.g. a fatty acid, a long chain aliphatic alcohol or a partial ester derived from fatty acids and a hexitol or a hexitol anhydrides, for example, polyoxyethylene stearate, polyoxyethylene sorbitol monooleate, polyoxyethylene sorbitan monooleate etc. Suitable suspending agents are, for example, sodium carboxymethylcellulose, methylcellulose, sodium alginate etc.

The present agents can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to the peptides of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., Methods in Cell Biology, Volume XIV, Academic Press, New York, N.Y. (1976), p. 33 et seq.

The pharmaceutical formulation may also be administered parenterally (intravenous, intramuscular, subcutaneous or the like) in dosage forms or formulations containing conventional, non-toxic pharmaceutically acceptable carriers and adjuvants. The formulation and preparation of such compositions is well-known to those skilled in the art of pharmaceutical formulation.

For parenteral use, the pharmaceutical compositions according to the invention may comprise the thermogenic compounds in the form of a sterile injection. To prepare such a composition, the compounds are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution and isotonic sodium chloride solution. The aqueous formulation may also contain one or more preservatives, for example, methyl, ethyl or n-propyl p-hydroxybenzoate.

For the rectal application, suitable dosage forms for a composition according to the present invention include suppositories (emulsion or suspension type), and rectal gelatin capsules (solutions or suspensions). In a typical suppository formulation, the compounds are combined with an appropriate pharmaceutically acceptable suppository base such as cocoa butter, esterified fatty acids, glycerinated gelatin, and various water-soluble or dispersible bases like polyethylene glycols and polyoxyethylene sorbitan fatty acid esters. Various additives like, for example, enhancers or surfactants, may be incorporated.

For the nasal application, typical dosage forms for a composition according to the present invention include nasal sprays and aerosols for inhalation. In a typically nasal formulation, the active ingredients are dissolved or dispersed in a suitable vehicle. The pharmaceutically acceptable vehicles and excipients and optionally other pharmaceutically acceptable materials present in the composition such as diluents, enhances, flavoring agents, preservatives, etc., are all selected in accordance with conventional pharmaceutical practice in a manner understood by the persons skilled in the art of formulating pharmaceuticals.

The pharmaceutical compositions according to the invention may also be administered topically on the skin for percutaneous absorption in dosage forms or formulations containing conventionally non-toxic pharmaceutically acceptable carriers and excipients including microspheres and liposomes. The formulations include creams, ointments, lotions, liniments, gels, hydrogels, solutions, suspensions, pastes, plasters and other kinds of transdermal drug delivery systems. The pharmaceutically acceptable carriers or excipients may include emulsifying agents, antioxidants, buffering agents, preservatives, humectants, penetration enhancers, chelating agents, gel-forming agents, ointment bases, perfumes and skin protective agents.

Examples of emulsifying agents are naturally occurring gums, e.g., gum acacia or gum tragacanth, naturally occurring phosphatides, e.g., soybean lecithin and sorbitan monooleate derivatives.

Examples of antioxidants are butylated hydroxy anisole (BHA), ascorbic acid and derivatives thereof, tocopherol and derivatives thereof and cysteine.

Examples of preservatives are parabens and benzalkonium chloride.

Examples of humectants are glycerin, propylene glycol, sorbitol and urea.

Examples of penetration enhancers are propylene glycol, DMSO, triethanolamine, N,N-dimethylacetamide, N,N-dimethylformamide, 2-pyrrolidone and derivatives thereof, tetrahydrofurfuryl alcohol and AZONE®.

Examples of chelating agents are sodium EDTA, citric acid and phosphoric acid.

Examples of gel forming agents are Carbopol, cellulose derivatives, bentonit, alginates, gelatin and PVP.

Examples of ointment bases are beeswax, paraffin, cetyl palmitate, vegetable oil, sorbitan esters of fatty acids (Span), polyethyleneglycols, and condensation products between sorbitan esters of fatty acids and ethylene oxide, e.g., polyoxyethylene sorbitan monooleate (Tween).

The formulation and preparation of the above-mentioned compositions is well-known to those skilled in the art of pharmaceutical formulation. Specific formulation can be found in "Remington's Pharmaceutical Sciences" incorporated herein by reference.

In one aspect the present invention relates to a method for treatment of overweight or obesity in individuals, in particular in humans or for reducing the adipose tissue mass/lean mass body mass ratio of an individual, in particular a human or a domestic animal.

In the present context the term "over eight" is used as an indication of a body with a weight exceeding the "desirable weight", whereas the term "obesity" is used when the body weight is 20% or more above the "desirable weight". Desirable weights for humans are given by the Council on Scientific Affairs defining the desirable weights for humans according to Metropolitan Height and Weight Tables as the midpoint of the range of the medium-frame individuals.

In another aspect, the present invention relates to a method for the treatment of diseases that are complications to overweight or obesity. These diseases or conditions include, for example, diabetes mellitus type II, hypercholesterolemia, hypertriglyceridaemia and hypertension.

In another aspect, the present invention also relates to a method of reducing adipose tissue mass/lean body mass ratio or treating overweight or obesity or complications thereof by means of subjecting the individuals to a diet regimen. The diet regimen into which the individuals may be subjected in connection with the administration of compositions of the present invention may include a low carbohydrate, a low fat and a low energy regimen, e.g., a diet of from 800-2500 kcal/day.

Veterinary Use

The NPY $Y_4$ receptor agonists including pancreatic polypeptide (PP), analogs thereof, and peptide fragments of PP, e.g. PP(32-36), and analogs thereof such as those of compounds (I-III), either alone or in combination with NPY $Y_2$ receptor agonists including peptide YY (PYY) (3-36), analogs thereof and to peptide fragments of PYY(3-36), e.g. PYY(22-36) and PYY(25-36), and analogs thereof such as those of compounds (IV-V), can also be administered to domestic animals in order to improve the performance of the animal (daily weight gain and feed utilization) or to improve carcass quality or both. Carcass quality is generally improved when the fat tissue mass/lean mass body mass ratio is decreased, i.e., when the body content of meat is increased e.g., at the expense of the body content of fat.

The improvements in performance and carcass quality are suggested to be caused by a reduced fat accretion and/or by an increased skeletal muscle accretion. In growing animals, the amount of lipid present is suggested to be governed by the relative rates of lipolysis and lipogenesis. Stimulation of lipolysis and/or inhibition of lipogenesis in fat tissue may lead to a reduced fat accretion. In vivo and in vitro studies with both pigs and ruminants may indicate that certain beta agonists stimulate lipolysis and inhibit lipogenesis in fat tissue leading to a reduced fat accretion.

Administration to an animal of the compositions according to the present invention may be useful in order to increase the lean body mass at the expense of body fat, particularly in domestic animals like pigs, hogs, cattle, sheep and poultry. The composition may be given in admixture with the feed in a suitable dose corresponding to the size of the animal.

Peptide Synthesis

The peptides of the present invention can be synthesized by any suitable method, such as by exclusively solid-phase techniques, by partial solid-phase techniques, by fragment condensation or by classical solution addition. A detailed description of certain of these methods is contained in "The Peptides, Vol. 1", Gross and Meinenhofer, Eds., Academic Press, New York, 1979. Coupling methods employed include the carbodiimide method (1,3-dicyclohexylcarbodiimide [DCC], 1-(3-dimethylaminopropyl-3-ethylcarbodiimide hydrochloride [EDCl]) with the option of racemization preventing additives (1-hydroxybenzotriazole [HOBT]), the mixed anhydride method, the azide method, the acid chloride method, the symmetrical anhydride method, the use of bis(2-oxo-3-oxazolidinyl)phosphinic chloride (BOP-Cl), and the active ester method (N-hydroxysuccinimide esters, 4-nitrophenol esters, 2,4,5-trichlorophenol esters, and the like). The synthesis of the PYY analogs of U.S. Pat. Nos. 5,604,203, and 6,046,167 to Balasubramaniam is fully disclosed therein, which is hereby incorporated by reference herein, and further is generally discussed below.

The techniques of exclusively solid-phase synthesis are set forth in the textbook "Solid-Phase Peptide Synthesis" Stewart & Young, Freeman & Co., San Francisco, 1969, and are exemplified by the disclosure of U.S. Pat. No. 4,105,603, issued Aug. 8, 1978 to Vale et al. The fragment condensation method of synthesis is exemplified in U.S. Pat. No. 3,972,859 (Aug. 3, 1976). Other available syntheses are exemplified by U.S. Pat. No. 3,842,067 (Oct. 15, 1974) and U.S. Pat. No. 3,862,925 (Jan. 28, 1975). All of the above references are incorporated herein by reference.

Synthesis by the use of recombinant DNA techniques, for purposes of this application, should be understood to include the suitable employment of a structural gene coding for peptides, or peptide fragments, to transform a microorganism, using an expression vector including a promoter and operator together with such structural gene, and causing such transformed microorganism to express the peptide or such a synthetic peptide fragment. A non-human animal may also be used to produce the peptide by gene-farming using such a structural gene in the microinjection of embryos as described in U.S. Pat. No. 4,870,009 issued Sep. 26, 1989, incorporated herein by reference.

When the peptides are not prepared using recombinant DNA technology, they are preferably prepared using solid phase synthesis, such as that described by Merrifield, J. Am. Chem. Soc., 85, p 2149 (1964), although other equivalent chemical syntheses known in the art can also be used as previously mentioned. Solid-phase synthesis is commenced from the C-terminus of the peptide by coupling a protected alpha-amino acid to a suitable resin as generally set forth in U.S. Pat. No. 4,244,946 issued Jan. 21, 1981 to Rivier et al., the disclosure of which is incorporated herein by reference. A starting material for analogs of the present invention can, for example, be prepared by attaching alpha-amino- and side-chain-protected Tyr to a BHA resin.

The compounds of the invention may be prepared by stepwise coupling of the amino acids or by coupling together fragments of dipeptide length or greater. Thus, the free carboxylic acid moiety from one amino acid or peptide fragment is activated and allowed to condense with the free nitrogen group of the second amino acid or peptide fragment. The coupling reactions are conducted in solvents such as methylene chloride ($CH_2Cl_2$), tetrahydrofuran (THF), dimethylformamide (DMF) or other such solvents.

During the coupling process, the non-participating carboxylic acids or amines on the reacting set of amino acids or peptide fragments are protected by a protecting group that can be selectively removed at a later time if desired. A detailed description of these groups and their selection and chemistry is contained in "The Peptides, Vol. 3", Gross and Meinenhofer, Eds., Academic Press, New York, 1981, incorporated herein in its entirety by reference. Thus, useful protective groups for the amino group are benzyloxycarbonyl (Cbz), t-butyloxycarbonyl (t-BOC), 2,2,2-trichloroethoxycarbonyl (Troc), t-amyloxycarbonyl, 4-methoxybenzyloxycarbonyl, 2-(trichlorosilyl)ethoxycarbonyl, 9-fluorenylmethoxycarbonyl (Fmoc), phthaloyl, acetyl (Ac), formyl, trifluoroacetyl, and the like.

Examples of useful protective groups for the carboxylic acid include esters, such as methyl, ethyl, benzyl, t-butyl, 2,2,2-trichloroethyl, allyl, 4-nitrobenzyl, and the like. Removal of these protecting groups may be accomplished selectively by employing various acid or base catalyzed hydrolytic, hydrogenolytic, thermal or dissolving metal conditions.

Generally, peptides will be synthesized by stepwise solid phase methodology developed by using an automated Applied Biosystem Model 430A peptide synthesizer. Tertiary butyloxy-carbonyl (Boc) amino acids with benzyl or halobenzyl based side chain protecting groups (Asp & Glu with Obzl or OcHex; Ser & Thr with Bzl: Cys with pMcBzl; Tyr with 2BrZ; Lys with 2ClZ; Arg with Tos; His with Boom; Trp with CHO) will be used in conjunction with phenylacetamidomethlyl (PAM) resin. In the case of the synthesis of peptide amides, benzyldrylamine (BHA) or paramethylbenzylhydrylamine (MBHA) will be used instead of PAM resin.

Boc-aminoacid-PAM-resin, using Boc-aminoacyloxy-methyl-phenylacetic acid and aminomethyl resin, is available commercially. The Boc-aminoacid-PAM-resin thus prepared eliminates the possibility of chain termination by tri-fluoroacetylation. Attachment to BHA or MBHA resin will be performed by way of preformed symmetrical anhydride.

Coupling and deprotection functions are generally carried out automatically by the instrument. The standard program provided by the manufacturers are modified to incorporate a double coupling procedure, first in DMF and then in $CH_2Cl_2$. Altering the polarity of the solvents improves the coupling. All amino acids, except Asn, Gln and Arg, will generally be coupled as preformed symmetrical anhydrides. Asn, Gln and Arg are double coupled as preformed 1-hydroxy-benzotriazole esters to avoid side reactions. Resin samples taken during these reactions may be assayed by quantitative procedure to determine the degree of coupling. Other standard cleaving reagents and conditions for removal of specific alpha-amino protecting groups may be used as described in Schroder & Lubke, "The Peptides" Vol. 1, pp 72-75 (Academic Press 1965), incorporated herein in its entirety by reference.

In the case of coupling unusual amino acids, suitable conditions (solubility, coupling times) will be first developed before using in automated mode. In some cases these couplings will be carried out manually (eg: pseudopeptides, N-Me-amino acids). Pseudopeptide bonds will be incorporated by the methods described earlier. The t-Boc-amino acid aldehyde will be obtained by reducing N-methoxy-N-methylamide derivatives of Boc-amino acids with $LiAlH_4$. The aldehyde obtained will be reacted immediately with the a-amino group of the peptide attached to the resin in DMF containing 1.0% HOAC in the presence of an equivalent amount of $NaaBH_3CON$. At the end of the reaction, the presence of secondary amine is tested for with ninhydrin (wine-red color). The secondary amine formed will then be blocked by reacting with 2 equivalents of Z(2-Cl)OSU, 2 equivalents of HOBT, and 4 equivalents of diisopropylethyamine until ninhydrin gives a yellow color. This way the formation of branched peptide is prevented. Coupling of sterically hindered amino acids (eg: N-Me-amino acids, CαeLeu, Aib) will be effected by a HOAT or HATU which has been shown to be superior to BOP/HOBT.

For the final cleavage, the N-α-Boc group and the Nin-CHO will be first removed with 50% $TFA/CH_2Cl_2$ and 20% piperidine-DMF from the protected peptide resin before detaching the target peptide using HF containing p. cresol (5%). If Cys and Met are present, p. thicresol (2.5%) will also be added to the HF reaction mixture. If problems are encountered during the standard HF method, then the "low/high" HF procedure will be used.

The materials are then purified. After initial fractionation on Sephadex G-25, the peptide material will be subjected to reversed phase high performance liquid chromatography (RPLC) on $C_{18}$ Vydac columns. However, peptides may be first subjected to ion exchange chromatography before RPLC, depending upon the heterogeneity of the crude peptide. The homogeneity of the purified product may be confirmed by analytical RPLC using two different solvent systems, amino acid analysis, complete sequencing, and mass spectral analysis.

For analysis, the peptide resins are hydrolyxed using 12N HCl/HOAc/phenol (2:1:1) for 24 hours at 110° C. The free peptides are hydrolyzed for 24 hours in 6N HCl containing 0.1% phenol or 4N methane sulfonic acid at 110° C. and are quantified on a Waters Pico Tag system. Peptide hormones and fragments are then subjected to complete sequencing on an automated gas phase sequencer (Applied Biosystem, Model 470A).

For the production of a compound of the invention where any one or several of the constituent amino acids bear an N-allyl group, specifically methyl, the corresponding N-alkyl amino acid can be prepared via the method described by Benoiton (Can. J. Chem., 1977, 55:906) or Shuman ("Peptides: Proceedings of the 7th American Peptide Symposium", D. Rich, E. Gross, Eds., Pierce Chemical Co., Rockford, Ill. 1981, p 617), wherein the t-BOC- or Cbz-protected amino acid is treated with a base in the presence of a chelating agent such as a crown ether and then quenched with methyl iodide. An alternative method described by Freidinger (J. Org. Chem., 1983, 48:77), in which triethylsilane reduction of the oxazolidinone of an amino acid directly produces the N-methyl derivative may also be utilized.

The reduced carbonyl amide bond surrogates can be prepared in a manner similar to that described by Martinez (J. Med. Chem. 1987, 30:1366). The N-alpha-t-BOC protected amino acid (with appropriate protection of side chain functional groups) is converted to the 3,5-dimethylpyrazolide, which is then reduced with lithium aluminum hydride. The resulting aldehyde is then allowed to condense with an amino acid or peptide bearing a free amino terminus. Reduction of the Schiff base that is formed as a result of the condensation is accomplished using sodium cyanoborohydride to yield the desired compound having a reduced amide bond.

Functionalization of the epsilon-amino group of the lysine (Lys) or homologous (e.g., Orn) residue is achieved via activation of the acid fragment as the active ester (N-hydroxysuccinimide, 2,4,5-trichlorophenol, etc.) or, if no other free carboxylic acid function is present on the peptide, coupling using any of the methods mentioned above is applicable. In addition, the functionalization of the epsilon-amino group may be accomplished by reaction with various alkyl and aryl isocyanates, as well as alkyl and aryl isothiocyanates.

The sulfuric acid esterification of the phenolic residues may be conducted using a variety of known reagents such as the pyridine-sulfuric anhydride or the pyridine-sulfur trioxide complex. Use of pyridinium acetyl sulfate as described by Penke and Rivier ("Proceedings of the 8th American Peptide Symposium", V. Hruby, D. Rich, Eds., Pierce Chemical Company, Rockford, Ill.; 1983; p. 119), may also be applied to prepare the sulfuric acid ester derivative of the peptides.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptonate, glycerophosphate, hemisulfate, heptonate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, tosylate, and undecanoate. Also, the basic nitrogen-containing groups can be quaternized with such agents as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

The pharmaceutically acceptable salts of the present invention can be synthesized which contain a basic or acidic moiety by conventional chemical methods. Generally, the salts are prepared by reacting, the free base or acid with stoichiometric amounts or with an excess of the desired salt forming inorganic or organic acid or base in a suitable solvent or various combinations of solvents.

Examples of preferred salts are those with therapeutically acceptable organic acids, e.g., acetic, lactic, maleic, citric, malic, ascorbic, succinic, benzoic, or pamoic acid, as wells as polymeric acids and salts with inorganic acids such as the hydrohalic acids, e.g., hydrocholoric and sulfuric acids.

In addition, pseudopeptide bonds may, if desired, may be introduced at various positions, e.g., between amino acid residues A1-A2 or between residues A2-A3. Optically pure Boc-AA-CHO can be obtained in good yields and coupled directly to the —NH2 group of the peptide resin by published methods (Sasaki et al., *Peptides* 8:119-121, 1987; Fehrentz et al., *Synthesis* pp. 676-678, 1983). The secondary amine in the pseudopeptide bond is capped with Z(2-Cl). This is introduced by reacting the peptide resin with Z(2-Cl)-OSU (2 equiv.), HOBT (2 equiv.) and DIEA (4 equiv.) for 10-60 min. The red wine color of ninhydrin with secondary amine turns yellow at the end of capping.

Exemplary compounds of the present invention include:

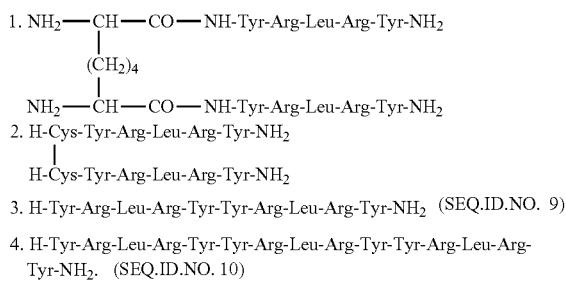

2. H-Cys-Tyr-Arg-Leu-Arg-Tyr-NH$_2$
   |
   H-Cys-Tyr-Arg-Leu-Arg-Tyr-NH$_2$

3. H-Tyr-Arg-Leu-Arg-Tyr-Tyr-Arg-Leu-Arg-Tyr-NH$_2$ (SEQ.ID.NO. 9)

4. H-Tyr-Arg-Leu-Arg-Tyr-Tyr-Arg-Leu-Arg-Tyr-Tyr-Arg-Leu-Arg-Tyr-NH$_2$. (SEQ.ID.NO. 10)

These compounds may be combined with NPY Y$_2$ receptor agonists including PYY(3-36), analogs thereof, and peptide fragments of PYY(3-36), e.g. PYY(22-36) and PYY(25-36), and analogs thereof such as those of formulas (IV-V).

Other analogs of the invention can be prepared as above and tested for their biological activity effectiveness as antagonists or agonists using the methods described below and those commonly known in the art.

Functional Assays
Animals. Cell Lines and Cultures, and Reagents

Any suitable in vivo or in vitro system may be utilized to assay and test the effectiveness of the compounds of the invention, and combinations thereof as discussed above. Such assays may employ in vivo methods for evaluating physiological responses, e.g., blood pressure, renovascular function, feeding behavior, or circadian rhythm, or in vivo biochemical systems evaluating receptor binding in a suitable cell line, e.g., SK-N-MC (ATCC HBT 10) or SK-N-BE(2) (Barnes et al. *In Vitro*, 17: 619 631, 1981); or in isolated cells, e.g., cells isolated from the spleen, kidney, heart or brain. A number of in vivo and in vitro biochemical systems known to those skilled in the art are available for testing antagonists to hypothalamic NPY receptors, e.g. the Y-1, Y-2, and Y-3 receptor categories. Described below are assay methods which can be utilized with cell lines such as SK-N-MC and SK-N-BE2 or isolated cardiac membranes which possess the high-affinity hypothalamic NPY receptor sites. Other systems are also known for evaluating NPY antagonists to the hypothalamic NPY receptor, e.g. VSM cells (Sheikh et al., *Am. J. Physiol.* 260: G250 G257, 1991) and HEL cells (Motulsky et al. *Amer. J. Physiol.* 255: E880-E885, 1988); Y-2 receptor, e.g., kidney (Sheikh et al., *Am. J. Physiol* 26:F978-F984), spleen (Lunberg et al., *Eur. J. Pharmal.* 145:21-29, 1988), dorsal root ganglion (Bleakman et al., *Br. J. Pharmal.* 103:1781-1789, 1991) and hippocampal cells (Sheikh et al., *J. Biol. Chem.* 265:8304 8310, 1990); and Y-3 receptors, e.g., in cardiac ventricular membranes (Balasubramaniam et al., Peptides 11: 545-550, 1990), chromaffin cells, rat gastric mucosa (Michel, M. C., *Trends in Pharmol. Sci.* 12: 389-394, 1991) and brain stem.

In Vitro Biochemical Assays

The ability of the compounds of the invention, and combinations thereof as discussed above, to act as antagonists of NPY can be demonstrated by any number of methods known in the art. For example, the compounds can be shown to compete with iodinated neuropeptide Y for receptors using the methods described by Lundberg et al. (*Eur. J. Pharmol.* 145: 21-29, 1988); Gordon et al. (*J. Neurochemistry* 55:506-513, 1990); Walker et al. (*Mol Pharmacol.* 34:779 792, 1988); Balasubramaniam et al. (*Peptides* 10:1283-1286, 1989).

In one example demonstrating antagonists to hypothalamic NPY receptors, rat hypothalmus was isolated and the membranes were prepared for binding and adenylate cyclase studies according to standard methods (Unden et al. 1984. *Eur. J. Biochem* 145: 525-530; Westlind-Danielsson et al., *Neurosci. Lett.* 74: 237-242 (1987)). Displacement studies are performed in a total volume of 0.25 ml 20 mM HEPES buffer, pH 7.4, containing 1% bovine serum albumin, 0.1% bacitracin, 300 μm PMSF and 5 KIU/ml aprotinin. In a standard assay, 100 μg of membrane/tube is incubated in a shaking water bath at 24° C. for 45 min with [$^{125}$I-Tyr]-NPY (20,000 CPM) as described by Balasubramaniam et al., (*Peptides* 11: 545-550, 1990), in the presence of increasing concentrations of NPY (10 μOsM). At the end of incubation, 1.0 ml of iced cold buffer is added, centrifuged at 10,000×g for 10 min, and the supernatant removed by aspiration. The tube containing the pellet is counted for bound radioactivity in a micromedic gamma counter.

An example of assaying adenylate cyclase activity of hypothalamic and cerebral cortex membranes is now described.

Adenlyate cyclase activity of the hypothalamic and cerebral cortex membranes is determined by incubating 50 μg of membranes in a total volume of 0.20 ml Tris-HCμ 30 mM pH 7.4 buffer containing 150 mM NaCl, 8.25 mM MgCl2, 0.75 mM EGTA, 1.5 theophylline, 20 μg/ml aprotinin, 100 μg/ml bacitracin, 1 mg/ml bovine serume albumin, 1 mM ATP, 20 mM creatine phosphate, 1 mg/ml phosphocreatine kinase, 10 μM isopreternol, 10 μM GTP, and various concentrations of peptides (0-10 μM). After incubating the mixture at 35° C. for 15 min in a shaking water bath, the reaction is arrested by the addition of 100 μM EDTA and boiling for 3 min. cAMP is extracted and quantitated by radioimmunoassay. All the points in the binding and adenlyate cyclase are the means of at least three parallel experiments performed in duplicate.

In Vivo Assays

Any suitable in vivo model system can be used to evaluate the properties of the compounds of the invention, and combinations thereof as discussed above. Such models, without limitation, include those used to evaluate feeding and memory behavior (Flood et al., *Peptides* 10:963-966), and vasoconstriction and hypertension (Balasubramaniam et al. *Biochemm et Biophys Acta* 997: 176-188, (1989)).

Thus, in one example, feeding studies can be performed using Spraque Dawley rats (350-450 g) with paraventricular hypothalmic cannulae to investigate effects of PP, NPY, and/or PAW analogs (Chance et al., *Peptides* 10: 1283, 1286 (1989)).

The following Examples set forth preferred methods for synthesizing the analogs of PP and of fragments thereof, such as the pentapeptide analogs of formulas (I-III) of the present invention, as well as the analogs of PYY and of fragments thereof; such as those of formulas (IV-V), using the solid-phase technique which generally is in accordance with the procedure set forth in U.S. Pat. No. 4,415,558 to Vale, et al., issued Nov. 15, 1983, the disclosure of which is incorporated herein by reference.

EXAMPLES

Example I

Analogs of PP(32-36) and, more specifically, the pentapeptide parallel dimer,

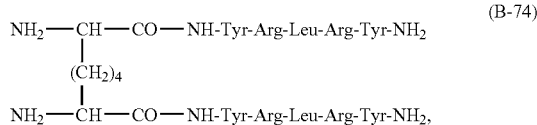

which includes the tetra-methylene spacer, was synthesized generally by standard stepwise t-Boc-solid phase methods and purified by reversed phase chromatography as is known in the art (J. Med. Chem. 2000, 49, 3420-3427).

More specifically, to obtain the parallel dimer, B-74, N-α-Boc-D/L-diamino-dicarboxylic acids (0.5 equiv) was coupled manually to the N-terminus of die protected pentapeptide peptide resin in the presence of equivalent quantities of DIC, HOBT, and DIEA. Free-peptide amides then were obtained by standard HF cleavage of the protected peptide-MBHA resin in the presence of about 5% p-cresol and about 2.5% thiocresol and purified by reversed phase chromatography.

Example II

To study the feeding patterns of animals treated with B-74, seven to eight week old C57BL/6 male mice (Harlan Laboratories, Indianapolis, Ind.) were individually housed in cages in a temperature controlled room (25° C.) under 12-hour light/dark cycles. Mice had free access to water and standard chow and were acclimatized to daily ip saline injections. After one week of acclimatizing, mice were fasted for 18 hours before the experiment, and saline (0.1 ml), hPP (10 nmol/mice), or B-74 (100 nmol/mice) in saline (0.1 ml) were injected intraperitoneally. Food was provided ten (10) minutes later, and the 2 and 4 hour food intake was monitored. Statistical significance was determined by ANOVA, with individual means being compared post-hoc by Tukey's corrected t-test.

Figure 1:
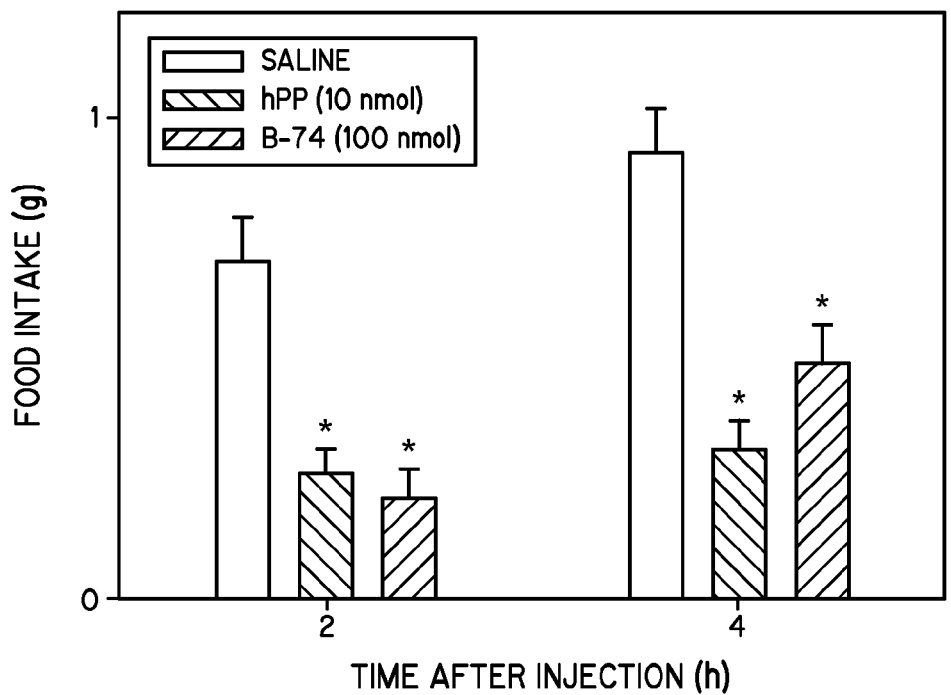
FIG. 1 is a graph representing the feeding patterns of animals treated with a PP(32-36) analog by intraperitoneal injection. The compounds tested include a control (saline), hPP.

The results are shown in FIG. 1. Specifically, intraperitoneal (ip) injections of PP (10 mmol/mice) and B-74 (100 nmol/mice) inhibited the 2 h and 4 h food intake to a greater extent than the control.

Example III

The PYY (22-36) analog, N-α-Ac[Nle$^{42,28}$,Trp$^{30}$,Nva$^{31}$, ψ$^{35/36}$]PYY(22-36)-NH$_2$ (SEQ. ID. NO. 7), referred to as B-48, wherein ψ is —CH2-NH—, was similarly synthesized by standard stepwise t-Boc-solid phase methods and purified by reversed phase chromatography as is known in the art according, and as referred to in Example I.

To further study the feeding patterns of animals treated with B-48, experiments were performed in seven to eight week old C57BL/6 male mice (Harlan Laboratories, Indianapolis, Ind.) after acclimatization of mice for one week. More specifically, in preliminary studies, overnight (18 h) fasted animals were injected (ip) with 0.1 ml of saline or saline (0.1 ml) containing various concentrations of B-48 (0.025, 0.050, 0.100 or 0.150 μmol/mice) (n=8-10 per group). The mice were provided with a known quantity of chow 10 min later. The food intake was monitored over 1-24 h. The results (not shown) revealed that a minimum dose of 0.050 μmol/mice of B-48 was required to exhibit significant inhibitory effects on food intake.

Example IV

To further compare the inhibitory effects of injecting (ip) 0.050 μmol of B-48 or B-74 alone or together (B-48+B-74) on the food intake by fasted mice, additional experiments were conducted.

Accordingly, to study the feeding patterns of animals treated with B-48 or B-74 alone or together (B-48+B-74), seven to eight week old C57BL/6 male mice (Harlan Laboratories, Indianapolis, Ind.) were individually housed in cages in a temperature controlled room (25° C.) under 12-hour light/dark cycles. The mice had free access to water and standard chow. After acclimatizing for one week, mice were fasted 18 hours before the experiment. The fasted animals were injected (ip) with 0.1 ml of saline or saline (0.1 ml) containing B-48 (0.050 μmol/mice) or B-74 (0.050 μmol/mice) alone or together, B-48+B-74 (0.100 μmol/mice, i.e. 0.050 μmol/mice per each compound), (n=8-10 per group). The mice were provided with a blown quantity of chow 10 minutes later. The food intake was monitored over 1-24 h. Statistical significance was determined by AN OVA, with individual means being compared post-hoc by Tukey's corrected t-test.

The results are shown in FIGS. 2 and 3. Specifically, treatment with B-74 or B-48 alone inhibited food intake to a greater extent than the control over the 24 h time period, while the combination treatment (B-48+B-74) inhibited food intake to a greater extent than either B-48 or B-74 taken alone. Table I below utilizes the data from FIGS. 2 and 3 to further illustrate the percentage inhibition of food intake by B-74 (0.05 μmol), B-48 (0.050 μmol), and B-74 (0.05 μmol)+B-48 (0.050 μmol) in the fasted mice at the 2 h, 4 h, 8 h, and 24 h marks.

TABLE I

| Percentage of Inhibition of Food Intake Compared to Saline | | |
|---|---|---|
| Hours after Injection | B-74 vs. (B-48 + B-74) | B-48 vs. (B-48 + B-74) |
| 2 | 35 vs. 85 | 39 vs. 72 |
| 4 | 26 vs. 63 | 30 vs. 54 |
| 8 | 14 vs. 44 | 16 vs. 30 |
| 24 | 7 vs. 24 | 7 vs. 20 |

Accordingly, as shown in FIGS. 2 and 3, and Table I, combined treatment of B-48+B-74 caused greater inhibition of food intake at all time points as compared to individual treatment with either B-74 or B-48, or the control.

While the present invention has been illustrated by the description of the various embodiments thereof and while the embodiments have been described in considerable detail, it is not intended to restrict or in any way limit the scope of the appended claims to such detail. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope of Applicants' general inventive concept. Various features of the invention are emphasized in the claims that follow.

What is claimed is:

1. A therapeutic composition capable of suppressing appetite, comprising a therapeutically effective amount of a compound together with a pharmaceutically acceptable carrier substance, the compound having the formula:

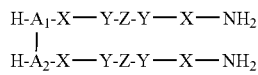

wherein:
each X, independently, is an aromatic amino acid other than Trp or any homologs of Trp;
each Y, independently, is an amino acid having a guanidino group;
each Z, independently, is an aliphatic amino acid;
A1 and A2, independently, are selected from Cys, Pen, Glu, Asp, Lys, and Dpr; and
wherein the compound optionally includes one or two pseudopeptide bonds where each pseudopeptide bond is independently selected from —$CH_2$—NH—, —$CH_2$—S—, —$CH_2$—$CH_2$—, —$CH_2$—O— and $CH_2$—CO—.

2. The composition of claim 1 wherein said composition is in the form of a liquid, pill, tablet, or capsule for oral administration to a subject.

3. The composition of claim 1 wherein said composition is in the form of a liquid for nasal, intravenous, subcutaneous, parenteral, or intraperitoneal administration to a subject to a subject.

4. A therapeutic composition capable of suppressing appetite comprising a therapeutically effective amount of a pentapeptide analog of PP(32-36) together with a pharmaceutically acceptable carrier substance, the pentapeptide analog of PP(32-36) having the formula:

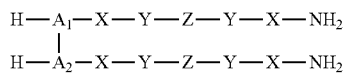

wherein:
each X, independently, is an aromatic amino acid other than Trp or any homologs of Trp;
each Y, independently, is an amino acid having a guanidino group;
each Z, independently, is an aliphatic amino acid;
A1 and A2, independently, are selected from Cys, Pen, Glu, Asp, Lys, and Dpr; and
wherein the compound optionally includes one or two pseudopeptide bonds where each pseudopeptide bond is independently selected from —$CH_2$—NH—, —$CH_2$—S—, —$CH_2$—$CH_2$—, —$CH_2$—O— and $CH_2$—CO—.

5. A therapeutic composition capable of suppressing appetite, comprising a therapeutically effective amount of a compound together with a pharmaceutically acceptable carrier substance, the compound having the formula:

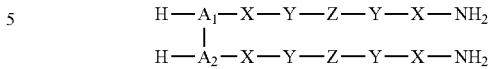

wherein:
each X, independently, is an aromatic amino acid chosen from Phe, Tyr, and His;
each Y, independently, is an amino acid having a guanidino group;
each Z, independently, is an aliphatic amino acid;
A1 and A2, independently, are selected from Cys, Pen, Glu, Asp, Lys, and Dpr; and
wherein the compound optionally includes one or two pseudopeptide bonds where each pseudopeptide bond is independently selected from —$CH_2$—NH—, —$CH_2$—S—, —$CH_2$—$CH_2$—, —$CH_2$—O— and $CH_2$—CO—.

* * * * *

UNITED STATES PATENT AND TRADEMARK OFFICE
CERTIFICATE OF CORRECTION

PATENT NO. : 8,729,227 B2  Page 1 of 3
APPLICATION NO. : 12/056600
DATED : May 20, 2014
INVENTOR(S) : Ambikaipakan Balasubramaniam It is certified that error appears in the above-identified patent and that said Letters Patent is hereby corrected as shown below:

In the Specification:

Column 2,
Line 18 reads "-Gfu-" and should read -- -Glu- --.

Column 4,
Line 59 reads "porcine PPY:" and should read -- porcine PYY: --.

Column 5,
Line 48 reads "one" and should read -- One --.

Column 6,
Line 34 reads "pseudopeplide bonds" and should read -- pseudopeptide bonds --.
Line 67 reads "-$C_2$-" and should read -- -$CH_2$- --.

Column 7,
Line approx. 26 reads "-ArgTyr-" and should read -- -Arg-Tyr- --.
Line 55 reads "($C_6$-$C_{18}$)acyl," and should read -- ($C_6$-$C_{18}$)aryl, --.

Column 8,
Line approx. 12 reads "Tip Nle," and should read -- Trp, Nle, --.

Column 9,
Line 7 reads "A" and should read -- $A^{28}$ --.
Line approx. 11 reads "Len," and should read -- Leu, --.
Line approx. 26 reads "NV" and should read -- Ψ --.

Column 10,
Line approx. 51 reads "one" and should read -- One --.

Signed and Sealed this
Fourteenth Day of October, 2014

Michelle K. Lee
*Deputy Director of the United States Patent and Trademark Office*

CERTIFICATE OF CORRECTION (continued)
U.S. Pat. No. 8,729,227 B2

Column 10,
Line approx. 58 reads "oil" and should read -- on --.

Column 11,
Line approx. 16 reads "selected from "-CH-"" and should read -- selected from -$CH_2$- --.
Line approx. 17 reads "-$C_2$-" and should read -- -$CH_2$- --.

Column 12,
Line 67 reads "Trp Nle," and should read -- Trp, Nle, --.

Column 13,
Line 6 reads "Lys-F-" and should read -- Lys-ε- --.
Line approx. 17 reads "[$Trp^3$]" and should read -- [$Trp^{30}$] --.
Line approx. 19 reads "-CH2-" and should read -- -$CH_2$- --.

Column 14,
Lines 23-24 read "-N-HR (where R is U," and should read -- -NH-R (where R is H, --.
Line 28 reads "(where R is U," and should read -- (where R is H, --.
Line 33 reads "-NH," and should read -- -$NH_2$, --.
Line 35 reads "-CH2NH-." and should read -- -$CH_2$-NH- --.

Column 15,
Line 55 reads "below, All" and should read -- below. All --.

Column 16,
Line 32 reads "Tcc=tetrahydrocarbolcnecarboxylic" and should read
-- Tcc=tetrahydrocarbolenecarboxylic --.

Column 18,
Line 9 reads "body weight general health," and should read -- body weight, general health, --.
Line 13 reads "suffice When" and should read -- suffice. When --.
Lines 27-28 read "administer a particular compounds," and should read -- administer particular compounds, --.
Line 64 reads "provide" and should read -- provides --.

Column 19,
Lines 3-4 read "and a hexitol or a hexitol anhydrides," and should read -- and a hexitol or hexitol anhydrides, --.
Line 29 reads "is" and should read -- are --.
Line 56 reads "typically" and should read -- typical --.
Line 61 reads "enhances," and should read -- enhancers, --.

Column 20,
Line 37 reads "is" and should read -- are --.
Line 46 reads "over eight" and should read -- "overweight" --.

CERTIFICATE OF CORRECTION (continued)

Column 22,
Line 56 reads "pMcBzl;" and should read -- pMeBzl; --.
Line 57 reads "His with Boom;" and should read -- His with Bom; --.

Column 23,
Line 3 reads "are" and should read -- is --.
Line 31 reads "diisopropylethyamine" and should read -- diisopropylethylamine --.
Line 55 reads "hydrolyxed" and should read -- hydrolyzed --.

Column 25,
Line 4 reads "bonds may, if desired, may be" and should read -- bonds may, if desired, be --.

Column 27,
Line approx. 55 reads "[Nle$^{42,28}$," and should read -- [Nle$^{24,28}$, --.

Column 28,
Line 26 reads "blown" and should read -- known --.
Line 65 reads "Applicants'" and should read -- Applicant's --.

In the Claims:

Column 34,
Line 53 reads "A1 and A2," and should read -- $A_1$ and $A_2$, --.
Lines 64-65 read "to a subject to a subject." and should read -- to a subject. --.

Column 35,
Line approx. 16 reads "A1 and A2," and should read -- $A_1$ and $A_2$, --.

Column 36,
Line approx. 16 reads "A1 and A2," and should read -- $A_1$ and $A_2$, --.

UNITED STATES PATENT AND TRADEMARK OFFICE
CERTIFICATE OF CORRECTION

PATENT NO. : 8,729,227 B2  
APPLICATION NO. : 12/056600  
DATED : May 20, 2014  
INVENTOR(S) : Ambikaipakan Balasubramaniam Page 1 of 1

It is certified that error appears in the above-identified patent and that said Letters Patent is hereby corrected as shown below:

In the Specification

Column 1,

Lines 14-18 read "The U.S. Government has a paid-up license in this invention and the right in limited circumstances to require the patent owner to license others on reasonable terms as provided for by the terms of Grant/Contract No. GM47122-08S1 awarded by the National Institutes of Health." and should read -- This invention was made with government support under Contract No. GM47122-08S1 awarded by the National Institutes of Health. The government has certain rights in the invention." --.

Signed and Sealed this  
Twenty-fourth Day of March, 2015

Michelle K. Lee  
*Director of the United States Patent and Trademark Office*

SEQUENCE LISTING

<160> NUMBER OF SEQ ID NOS: 10

<210> SEQ ID NO 1
<211> LENGTH: 36
<212> TYPE: PRT
<213> ORGANISM: human neuropeptide Y
<220> FEATURE:
<221> NAME/KEY: MOD_RES
<222> LOCATION: (36)..(36)
<223> OTHER INFORMATION: AMIDATION

<400> SEQUENCE: 1

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 2
<211> LENGTH: 36
<212> TYPE: PRT
<213> ORGANISM: porcine peptide YY

<400> SEQUENCE: 2

Tyr Pro Ala Lys Pro Glu Ala Pro Gly Glu Asp Ala Ser Pro Glu Glu
1               5                   10                  15

Leu Ser Arg Tyr Tyr Ala Ser Leu Arg His Tyr Leu Asn Leu Val Thr
            20                  25                  30

Arg Gln Arg Tyr
        35

<210> SEQ ID NO 3
<211> LENGTH: 36
<212> TYPE: PRT
<213> ORGANISM: human peptide YY

<400> SEQUENCE: 3

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 4
<211> LENGTH: 12
<212> TYPE: PRT
<213> ORGANISM: Artificial
<220> FEATURE:
<223> OTHER INFORMATION: synthesized by man
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (12)..(12)
<223> OTHER INFORMATION: AMIDATION

<400> SEQUENCE: 4

Arg His Tyr Leu Asn Trp Val Thr Arg Gln Arg Tyr
1               5                   10

```
<210> SEQ ID NO 5
<211> LENGTH: 12
<212> TYPE: PRT
<213> ORGANISM: Artificial
<220> FEATURE:
<223> OTHER INFORMATION: synthesized by man
<220> FEATURE:
<221> NAME/KEY: misc_feature
<223> OTHER INFORMATION: Reduced peptide bond between 11 and 12
      (-CH2-NH-)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (12)..(12)
<223> OTHER INFORMATION: AMIDATION

<400> SEQUENCE: 5

Arg His Trp Leu Asn Leu Val Thr Arg Gln Arg Tyr
1               5                   10

<210> SEQ ID NO 6
<211> LENGTH: 12
<212> TYPE: PRT
<213> ORGANISM: Artificial
<220> FEATURE:
<223> OTHER INFORMATION: synthesized by man
<220> FEATURE:
<221> NAME/KEY: misc_feature
<223> OTHER INFORMATION: Reduced peptide bond between 11 and 12
      (-CH2-NH-)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (12)..(12)
<223> OTHER INFORMATION: AMIDATION

<400> SEQUENCE: 6

Arg His Tyr Leu Asn Trp Val Thr Arg Gln Arg Tyr
1               5                   10

<210> SEQ ID NO 7
<211> LENGTH: 15
<212> TYPE: PRT
<213> ORGANISM: artificial
<220> FEATURE:
<223> OTHER INFORMATION: synthesized by man
<220> FEATURE:
<221> NAME/KEY: MISC_FEATURE
<223> OTHER INFORMATION: reduced peptide bond between 14 and 15
      (-CH2-NH-)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (7)..(7)
<223> OTHER INFORMATION: Nle
<220> FEATURE:
<221> NAME/KEY: MOD_RES
<222> LOCATION: (10)..(10)
<223> OTHER INFORMATION: Nva
<220> FEATURE:
<221> NAME/KEY: MOD_RES
<222> LOCATION: (15)..(15)
```

```
<223> OTHER INFORMATION: AMIDATION

<400> SEQUENCE: 7

Ala Ser Xaa Arg His Tyr Xaa Asn Trp Xaa Thr Arg Gln Arg Tyr
1               5                   10                  15

<210> SEQ ID NO 8
<211> LENGTH: 36
<212> TYPE: PRT
<213> ORGANISM: Artificial
<220> FEATURE:
<223> OTHER INFORMATION: human pancreatic peptide (PP)

<400> SEQUENCE: 8

Ala Pro Leu Glu Pro Val Tyr Pro Gly Asp Asn Ala Thr Pro Glu Gln
1               5                   10                  15

Met Ala Gln Tyr Ala Ala Asp Leu Arg Arg Tyr Ile Asn Met Leu Thr
            20                  25                  30

Arg Pro Arg Tyr
        35

<210> SEQ ID NO 9
<211> LENGTH: 10
<212> TYPE: PRT
<213> ORGANISM: Artificial
<220> FEATURE:
<223> OTHER INFORMATION: synthesized by man
<220> FEATURE:
<221> NAME/KEY: MOD_RES
<222> LOCATION: (10)..(10)
<223> OTHER INFORMATION: AMIDATION

<400> SEQUENCE: 9

Tyr Arg Leu Arg Tyr Tyr Arg Leu Arg Tyr
1               5                   10

<210> SEQ ID NO 10
<211> LENGTH: 15
<212> TYPE: PRT
<213> ORGANISM: Artificial
<220> FEATURE:
<223> OTHER INFORMATION: synthesized by man
<220> FEATURE:
<221> NAME/KEY: MOD_RES
<222> LOCATION: (15)..(15)
<223> OTHER INFORMATION: AMIDATION

<400> SEQUENCE: 10

Tyr Arg Leu Arg Tyr Tyr Arg Leu Arg Tyr Tyr Arg Leu Arg Tyr
1               5                   10                  15
```